United States Patent
Edelman

(10) Patent No.: US 8,216,163 B2
(45) Date of Patent: Jul. 10, 2012

(54) SYSTEM AND METHODS FOR AN INTERCHANGEABLE LUMBAR CONTRAST THERAPY PAD

(75) Inventor: Howard Edelman, San Francisco, CA (US)

(73) Assignee: VitalWear, Inc., South San Francisco, CA (US)

( * ) Notice: Subject to any disclaimer, the term of this patent is extended or adjusted under 35 U.S.C. 154(b) by 358 days.

(21) Appl. No.: 12/623,290

(22) Filed: Nov. 20, 2009

(65) Prior Publication Data

US 2010/0137765 A1 Jun. 3, 2010

Related U.S. Application Data

(63) Continuation-in-part of application No. 10/267,247, filed on Oct. 8, 2002, now Pat. No. 7,211,104, and a continuation-in-part of application No. 11/469,614, filed on Sep. 1, 2006, now Pat. No. 8,052,628.

(51) Int. Cl.
- *A61F 5/00* (2006.01)
- *A61F 5/01* (2006.01)
- *A61F 7/00* (2006.01)

(52) U.S. Cl. ............... 602/2; 602/19; 607/108
(58) Field of Classification Search ............... 602/2, 19; 607/108

See application file for complete search history.

(56) References Cited

U.S. PATENT DOCUMENTS

| | | | |
|---|---|---|---|
| 4,470,417 A * | 9/1984 | Gruber | 607/108 |
| 4,702,235 A * | 10/1987 | Hong | 602/13 |
| 5,062,414 A * | 11/1991 | Grim | 602/19 |
| 5,411,541 A * | 5/1995 | Bell et al. | 607/104 |
| 5,695,452 A * | 12/1997 | Grim et al. | 602/6 |
| 6,374,440 B1 * | 4/2002 | Thim, Jr. | 5/633 |
| 6,551,347 B1 * | 4/2003 | Elkins | 607/104 |
| 7,211,104 B2 * | 5/2007 | Edelman | 607/104 |
| 8,052,628 B1 * | 11/2011 | Edelman et al. | 602/2 |
| 2005/0043655 A1 * | 2/2005 | Schenck | 601/15 |
| 2006/0052733 A1 * | 3/2006 | Schwenn et al. | 602/19 |
| 2006/0122547 A1 * | 6/2006 | Stewart et al. | 602/19 |
| 2007/0179417 A1 * | 8/2007 | Schwenn et al. | 602/19 |
| 2009/0105626 A1 * | 4/2009 | Lemons | 602/61 |
| 2009/0204042 A1 * | 8/2009 | Park | 602/19 |
| 2010/0049109 A1 * | 2/2010 | Stewart, III | 602/19 |
| 2010/0137765 A1 * | 6/2010 | Edelman | 602/14 |
| 2010/0168630 A1 * | 7/2010 | Cropper et al. | 602/19 |
| 2010/0204629 A1 * | 8/2010 | Specht | 602/19 |
| 2010/0262056 A1 * | 10/2010 | Lusky et al. | 602/19 |
| 2010/0268138 A1 * | 10/2010 | Summit et al. | 602/16 |
| 2010/0268140 A1 * | 10/2010 | Berlese | 602/19 |

* cited by examiner

*Primary Examiner* — Roy Gibson
*Assistant Examiner* — Kaitlyn Smith
(74) *Attorney, Agent, or Firm* — Kang S. Lim

(57) ABSTRACT

The present invention relates to a spinal column brace system which includes a rigid support, an interchangeable therapy pad, and a front panel. The rigid support includes patches of hook material and also has straps connected to it. These straps are at least partially elastic and also include hook material pads on their ends. The interchangeable therapy pad, on the other hand, has one side covered in loop material, thereby allowing the therapy pad to be attached to the patches on the rigid support. The front panel is also covered in loop material, which may be used to couple to the hook material found on the straps. The therapy pad includes a thermal exchange bladder and a cushion layer. The thermal exchange bladder may be coupled to a contrast therapy system via an umbilical and fluid coupler. The contrast therapy system includes a hot and cold reservoir. A mixing valve may mix a selected ratio of the hot and cold fluids from the hot and cold reservoirs to make therapy fluid of a particular temperature. A fluid pump then delivers the therapy fluid to the thermal exchange bladder.

10 Claims, 33 Drawing Sheets

SYSTEM AND METHODS FOR AN INTERCHANGEABLE LUMBAR CONTRAST THERAPY PAD

CROSS REFERENCE TO RELATED APPLICATIONS

This is a continuation-in-part of U.S. application Ser. No. 10/267,247 filed on Oct. 8, 2002, entitled "Contrast Therapy System and Method", now U.S. Pat. No. 7,211,104, which is hereby fully incorporated by reference.

This is also a continuation-in-part of U.S. application Ser. No. 11/469,614 filed on Sep. 1, 2006, entitled "Spinal Column Brace for a Contrast Therapy System", now U.S. Pat. No. 8,052,628 which is hereby fully incorporated by reference.

BACKGROUND OF THE INVENTION

The present invention relates to spinal column braces, and more particularly, to spinal column braces assemblies which incorporate bladders and which are adapted for use in a thermal or contrast therapy system, or medical thermal therapy system. The bladder elements of the present invention enable the user to obtain a tightly controlled and consistent temperature or contrast therapy, along with support, pressure and/or compression therapy.

Back and spinal impairments affected an estimated 18.454 million people in the United States in 1995. This accounts for roughly 70.5 back or spinal impaired people per 1000 people. Back and spinal impairments account for over half of the musculoskeletal impairments in the United States. Additionally, back and spinal impairments can be extremely debilitating and painful.

Spinal column braces, also referred to as back braces, are commonly utilized to alleviate pain, provide stability, increased mobility, and reduced healing time after injury, medical procedure or ailment. Conditions commonly requiring a spinal column brace include, but are not limited to, a stabilizing operation (e.g., spondylodesis), lumbar disk surgery, degenerative instability, Spondylolisthesis, spondylolysis, facet syndrome, lumbar spinal stenosis, symptomatic stenoses of the intervertebral lumbar foramina, fractures of the lower lumbar spine, tumors (metastases), and inflammation. Traditionally, spinal column braces provide support to the wearer by wrapping around the person's trunk. Spinal column braces are rigid or semi-rigid, providing external support, and by wrapping tightly around the trunk the abdominal cavity is compressed thereby providing internal support. The support provided by a spinal column brace alleviates compression on the wearer's spinal column, alleviating pain and allowing damaged tissue to properly heal and rehabilitate.

Additionally, numerous thermal therapy devices that apply external treatments to the body are known in the art. Thermal or contrast therapy devices deliver or remove heat to a given therapy area for an effective amount of time in order to achieve a desired therapeutic result. Contrast therapy devices are used to reduce swelling or to encourage healing after swelling has receded. They are also used to soothe muscle and joint pain through the application of heat and compression therapy. Application of heat or cold may be used to heal and rehabilitate injuries to bone, muscle, ligaments, tendons and skin. Cold therapy may be used to reduce swelling, decrease pain, and promote healing of injured tissue. Heat therapy can be used to relax joint tissue, such as ligaments and tendons, to increase range of motion. Thermal therapy can also be used after surgery to reduce pain and swelling and promote healing.

The potential effectiveness of a hot or cold treatment increases as the level of control for the treatment increases. In particular, the effectiveness depends on the ability to control the temperature of the treatment. If cold treatments are too cold, they may cause skin and tissue damage. Similarly, if hot treatments are too hot, they may burn or otherwise damage the recipient. The effectiveness of a therapy also is dependent on the ease in which the therapy may be applied. If it is difficult for a therapy recipient to self apply a therapy, the opportunity to receive therapy may be diminished. Furthermore, if therapies are complicated and/or uncomfortable, a therapy recipient is less likely to undergo the therapy, although it may be beneficial.

It is therefore apparent that an urgent need exists for an improved spinal column brace that integrates the added benefits of contrast therapy. This assembly would be able to provide a high level of spinal column support with the addition of a thermal therapy that may be very well regulated.

SUMMARY OF THE INVENTION

To achieve the foregoing and in accordance with the present invention, a system and methods for an interchangeable contrast therapy pad in a spinal support brace is provided. This system may be useful in conjunction with a thermal contrast therapy system to provide a temperature regulated fluid to the lumbar region of a user. Such systems are useful for providing effective spinal column support with integrated contrast thermal therapy.

The spinal column brace system includes a rigid support, an interchangeable therapy pad, and a front panel. The rigid support includes patches of hook material and also has straps connected to it. These straps are at least partially elastic and also include hook material pads on their ends.

The interchangeable therapy pad, on the other hand, has one side covered in loop material, thereby allowing the therapy pad to be attached to the patches on the rigid support. Additionally, the therapy pad includes a fluid bladder and a cushion layer and an umbilical connected to a fluid coupler. The cushion may include a plastic foam or elastomer. A mesh layer may exist on the surface of the therapy pad where the pad is to be fitted against the therapy site.

The front panel is also covered in loop material, which may be used to couple to the hook material found on the straps. In this way, the front panel may be placed on the wearer's stomach and the rigid support/therapy pad assembly may be placed on the wearer's back. The straps then wrap from the wearer's back to the front where they engage the front panel. This holds the brace firmly in place with the interchangeable therapy pad in a fitted position adjacent the spinal column therapy site of the wearer.

The front panel may also include a pocket for a rigid member. This can further increase the brace rigidity and therefore increase wearer support.

Additionally, the fluid bladder may be a thermal exchange bladder. Thus, the thermal exchange bladder may be coupled to the contrast therapy system via the umbilical and fluid coupler. The contrast therapy system includes a hot reservoir for holding a relatively hot fluid and a cold reservoir for holding a relatively cold fluid. A mixing valve may mix a selected ratio of the hot and cold fluids from the hot and cold reservoirs to make therapy fluid of a particular temperature. A fluid pump then delivers the therapy fluid to the thermal exchange bladder.

The pump may cause either constant or dynamic pressure within the thermal exchange bladder, depending upon whether steady compression or pulsating compression is desired on the therapy site.

All rigid materials may be contoured sheets of semi-rigid material less than five millimeters in thickness. Cutouts may also be made in the rigid materials to reduce overall weight.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, one embodiment will now be described, by way of example, with reference to the accompanying drawings, in which.

DETAILED DESCRIPTION OF THE INVENTION

The present invention will now be described in detail with reference to several embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention. The features and advantages of the present invention may be better understood with reference to the drawings and discussions that follow.

The present invention relates to therapeutic spinal column brace system, which includes an interchangeable contrast therapy pad. This embodiment of the spinal column brace with contrast therapy is configured to provide the user with a maximal level of mobility. The high degree of pad interchangeability enables the brace to be worn with both the therapy pad and/or with a basic compression and comfort pad.

Figure 7:
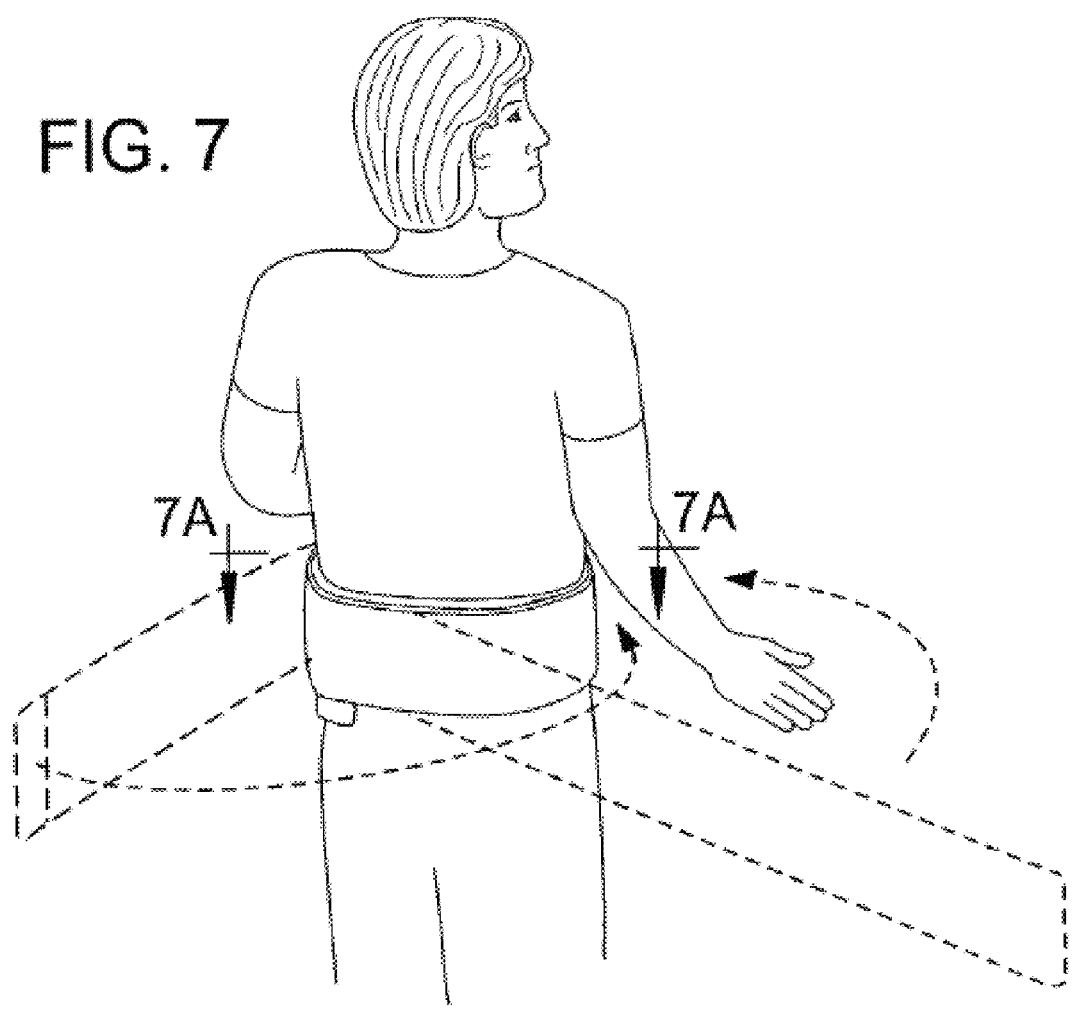
FIG. 7 is an isometric view of a therapy pad wrapped around a therapy recipient.
Figure 8:
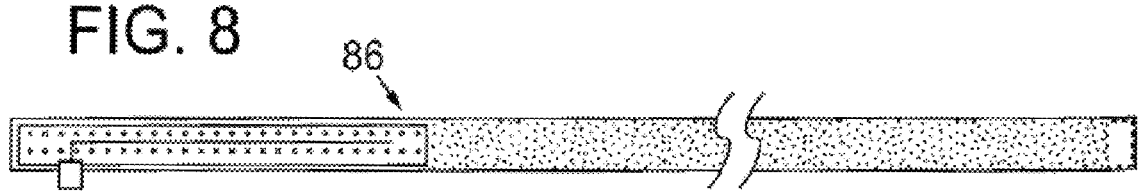
FIG. 8 is a plan view of a contrast therapy pad in accordance with an embodiment of the present invention.
Figure 9:
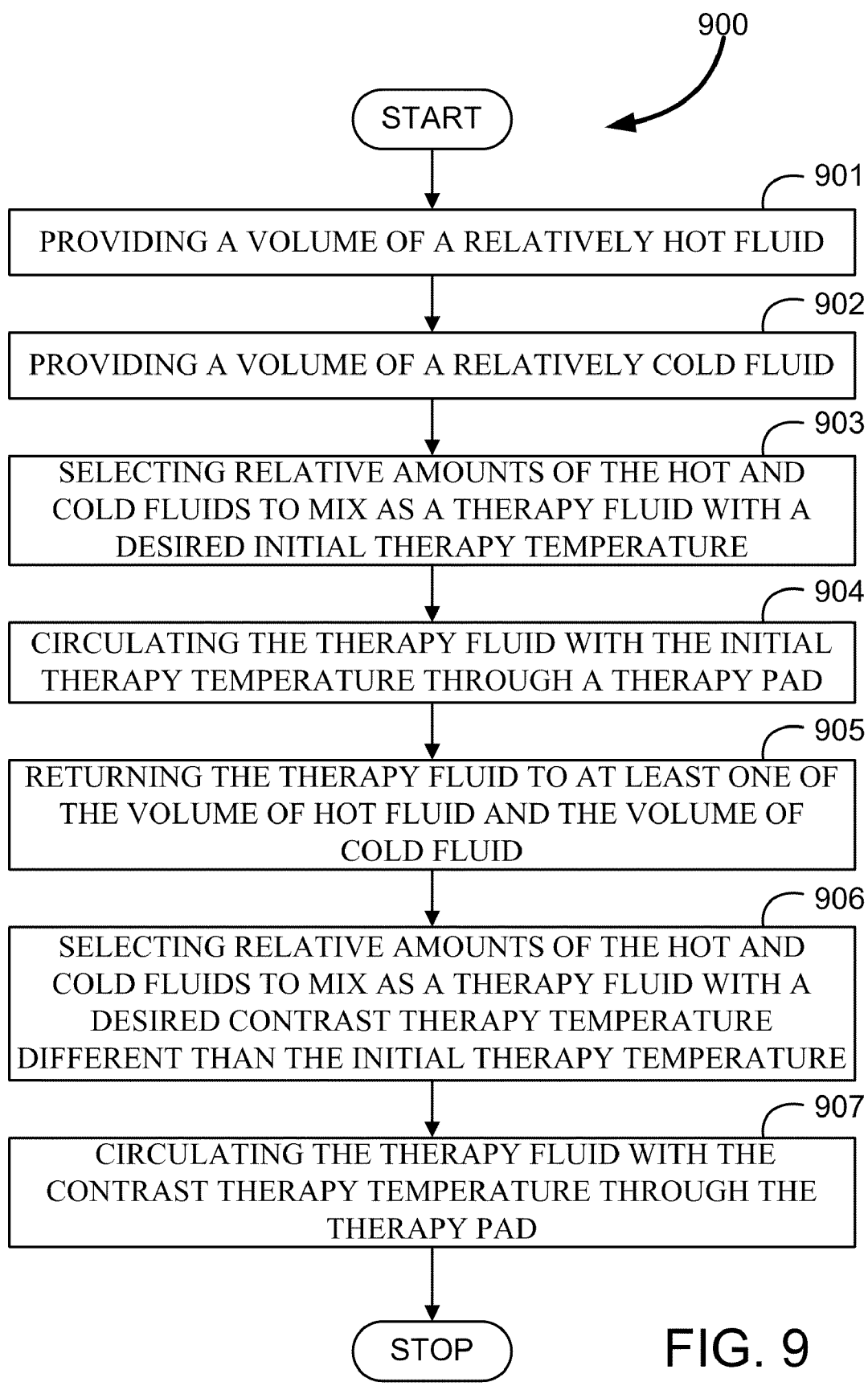
FIG. 9 is an illustration of a method for administering contrast therapy to a therapy recipient in accordance with an embodiment of the present invention.

To facilitate discussion, FIGS. 1 through 8 show various views of the present contrast therapy system. FIG. 9 provides an illustration of a method for providing contrast therapy to a therapy recipient. FIGS. 10 through 17D provide various views of a first Therapeutic Spinal Column Brace System at 1000. FIGS. 18A to 22 provide various views of a second spinal column brace system which facilitates interchangeability of contrast therapy pads as well as enhanced mobility.

Although useful for applying any combination of heat, cold, compression and support to a recipient for virtually any reason, the Therapeutic Spinal Column Brace System 1000 including Thermal Contrast Therapy Systems 10 described below demonstrates particular utility for treating sore, strained, arthritic, injured, post operable, heavily exercised, and/or otherwise taxed back and spinal regions. The contrast therapy system is described below in the context of providing "therapy" to a recipient, however, it should be understood that the Therapeutic Spinal Column Brace System 1000 including Thermal Contrast Therapy Systems 10 are equally well suited for providing any combination of heat, cold, compression and support for what may be considered non-therapeutic purposes.

As described herein, the Contrast Therapy System 10 is capable of imparting a desired therapy temperature to a Therapy Pad 22 or in the present invention a Thermal Exchange Layer 1010 or a Therapy Bladder 1800, which may be applied to a therapy recipient. The system is capable of shifting the therapy temperature between hot and cold temperatures very quickly, which has proven to be beneficial. The precise temperature may be set at any temperature between controlled maximum and minimum temperatures. Furthermore, the contrast therapy system may be designed as a relatively small portable unit, as shown at 30 of FIG. 1, which is both easy and inexpensive to operate. The Portable Unit 30 includes a Container 24 and a Lid Unit 28. The Lid Unit 28 includes a Dial 48 and Indicia 50 to aid in the temperature control of the contrast therapy. The Container 24 may include a Cold Reservoir 12 and an Open End 26 that the Lid Unit 28 may fit into.

As described herein, the first Therapeutic Spinal Column Brace System 1000 is capable of imparting support to a therapy recipient, and provides a medium for the Contrast Therapy System 10. The Therapeutic Spinal Column Brace System 1000 includes multiple layers that are secured around the torso of the therapy recipient. These layers include, from therapy site outward, the Thermal Exchange Layer 1010, a Compression Layer 1020, a Cushion Layer 1030 and an Outer Layer 1040. Alternatively, in some embodiment, an Amalgamated Bladder 1700 may be utilized to replace the Thermal Exchange Layer 1010 and Compression Layer 1020. The Thermal Exchange Layer 1010, or in another embodiment the Amalgamated Bladder 1700, may be coupled to the contrast therapy system Portable Unit 30 through a Fluidic Coupling Assembly 20.

Figure 12:
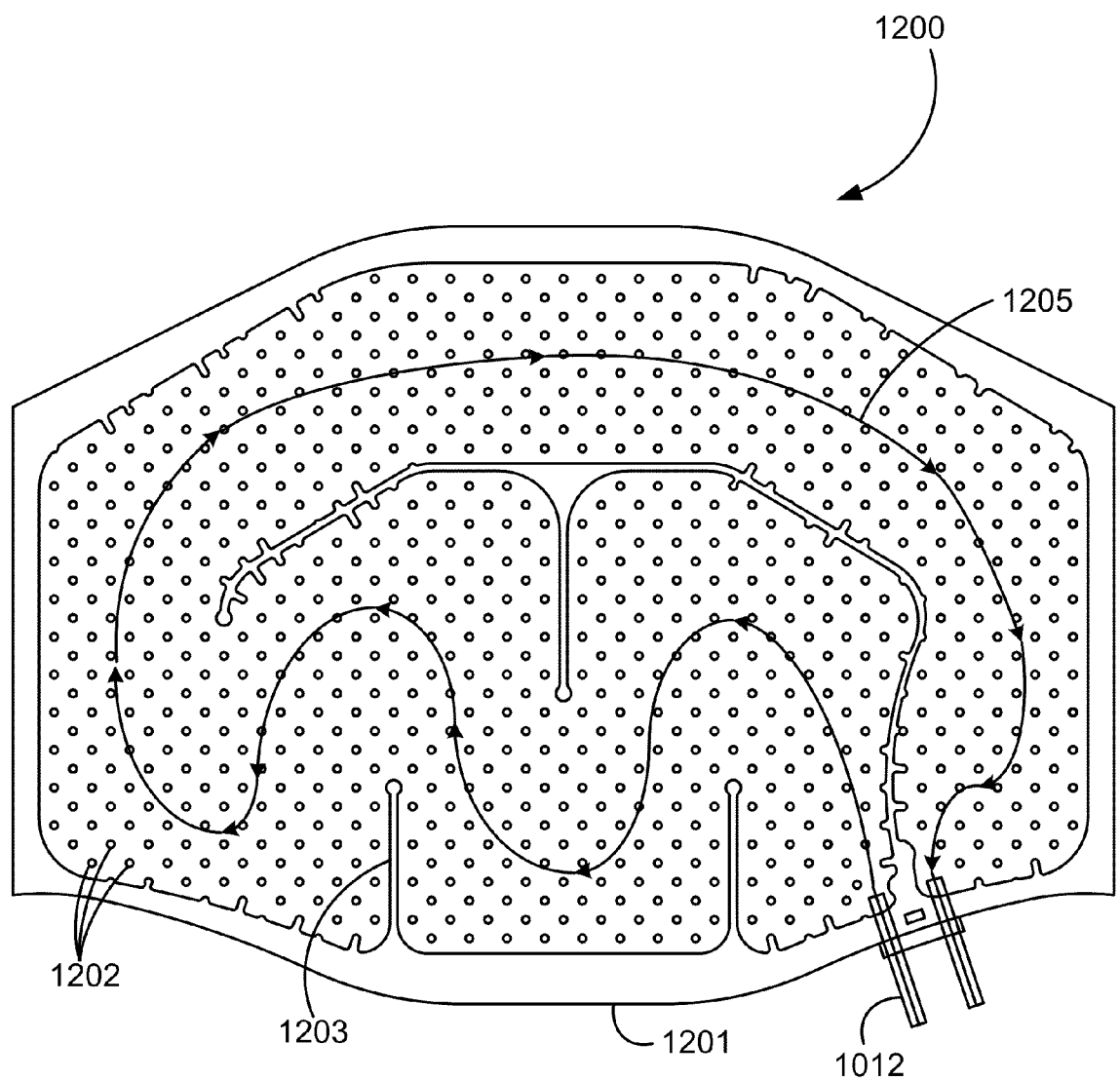
FIG. 12 shows an isometric view of a Thermal Exchange Bladder for use in a therapeutic spinal column brace system in accordance with an embodiment of the present invention.
Figure 13A:
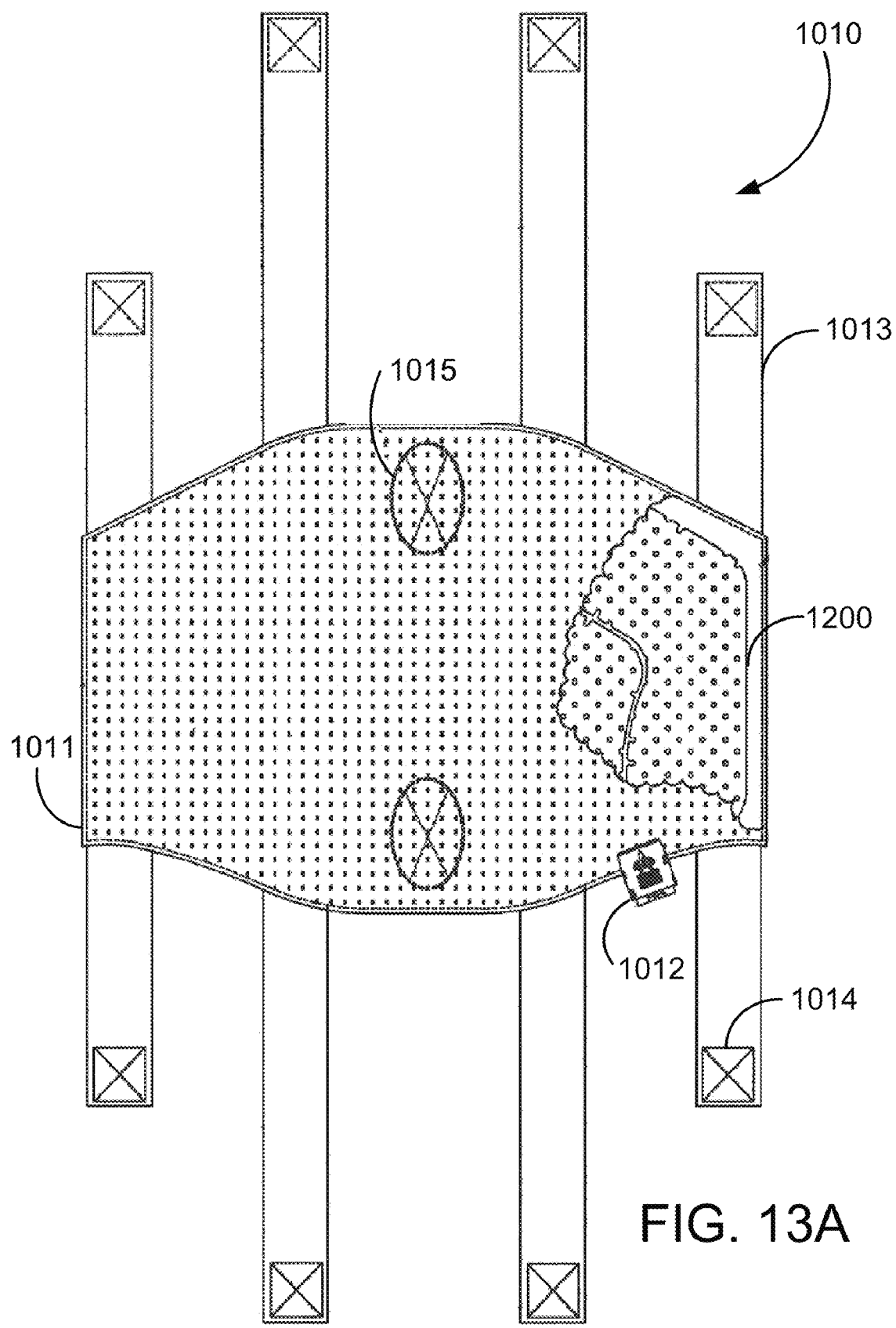
FIG. 13A shows a top plan cutaway view of a Thermal Exchange Bladder within a thermal exchange layer for use in a therapeutic spinal column brace system in accordance with an embodiment of the present invention.
Figure 13B:
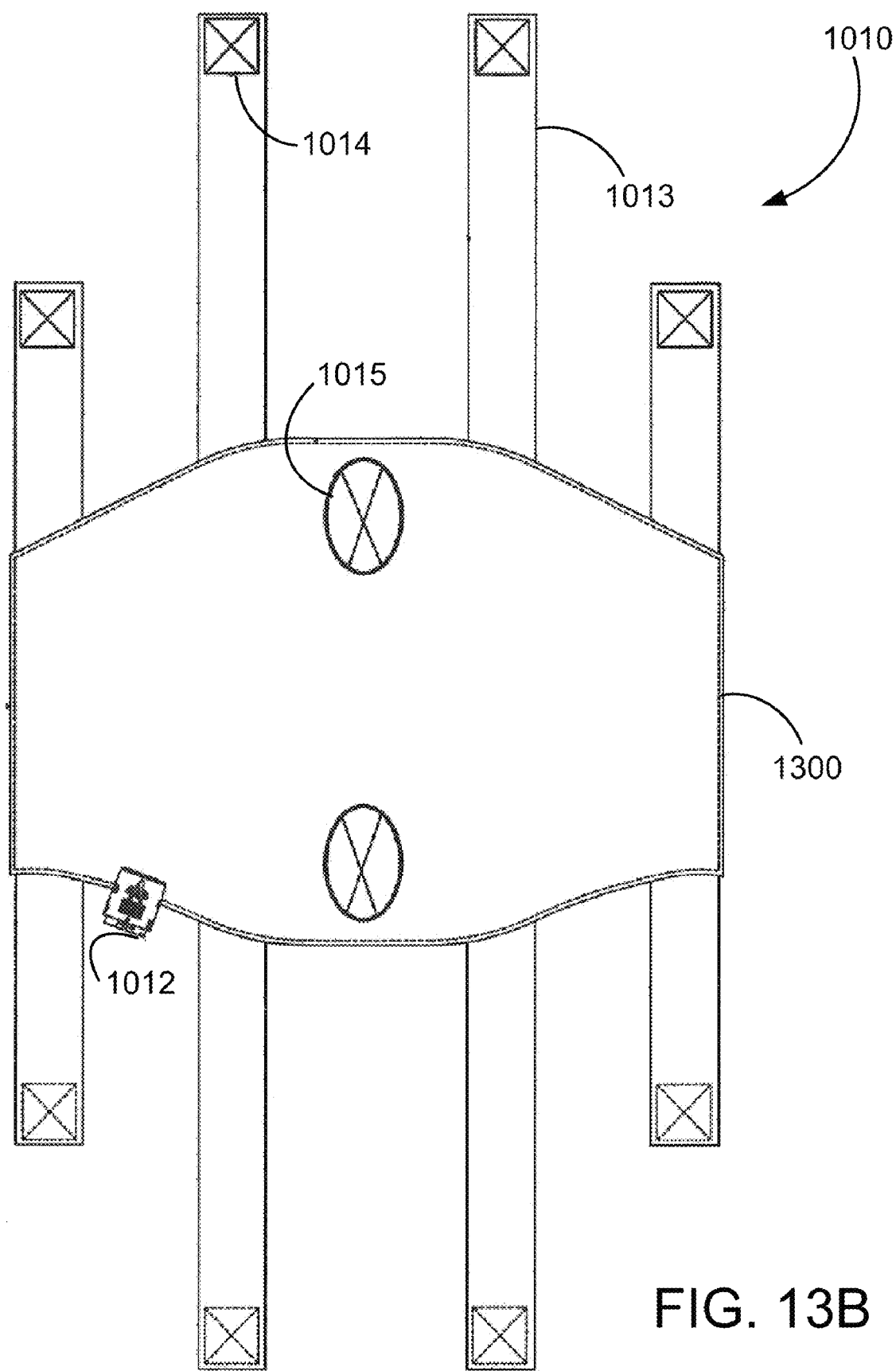
FIG. 13B shows a bottom plan view of a thermal exchange layer for use in a therapeutic spinal column brace system in accordance with an embodiment of the present invention.
Figure 13C:
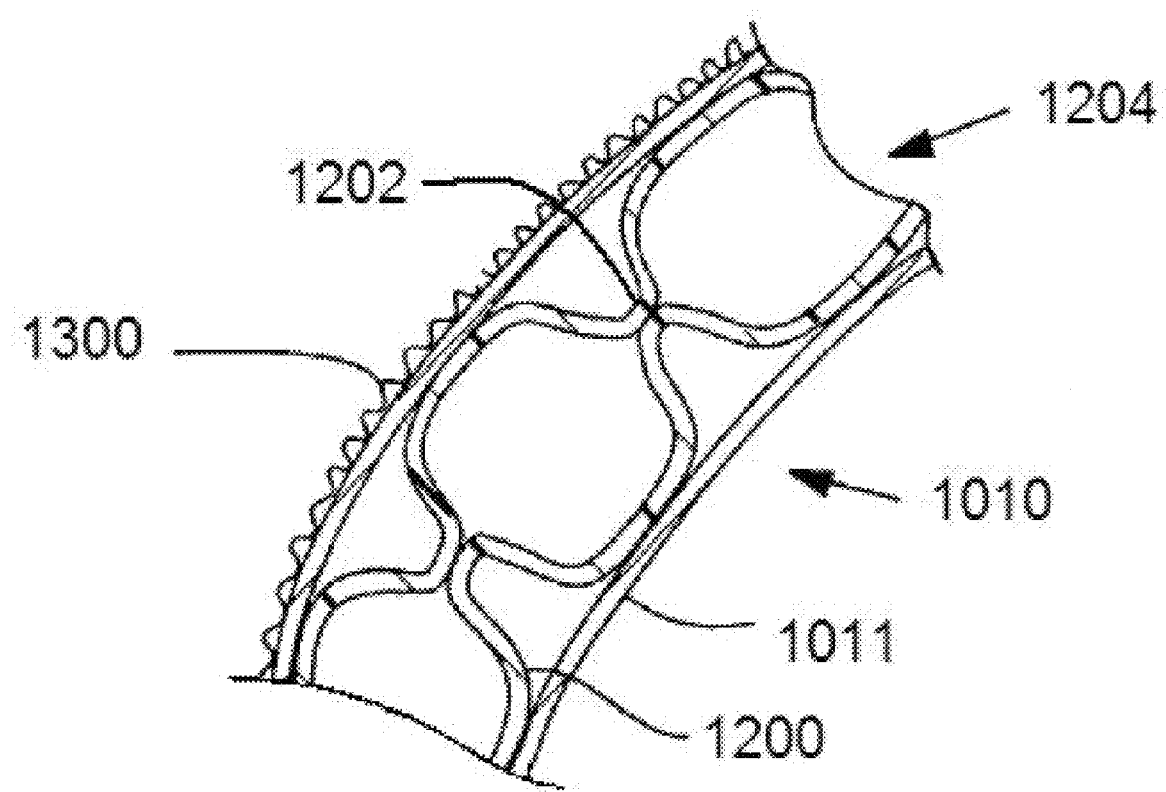
FIG. 13C is a cross-sectional view of a portion of the thermal exchange layer for use in a therapeutic spinal column brace system in accordance with an embodiment of the present invention.

Thermal Exchange Layer 1010, as seen in FIGS. 13A, 13B and 13C, includes an integrated Thermal Exchange Bladder 1200, seen in FIG. 12. The Thermal Exchange Layer 1010 has a face comprised of a Mesh 1011, or other efficient thermal exchange medium, to ensure rapid transference of temperature form the Thermal Exchange Layer 1010 to the therapy recipient. Additionally, the Thermal Exchange Layer 1010 may utilize Adjustable Elastic Straps 1013 for securing the Thermal Exchange Layer 1010 to the other layers of the Therapeutic Spinal Column Brace System 1010. Furthermore, Hook Material 1015 may be utilized to secure the Thermal Exchange Layer 1010 to a Compression Layer 1020 by releasably receiving complementary loop material on the Compression Layer's 1020 Surface 1021.

The system is also capable of applying compressive force to a therapy recipient through Compression Layer 1020, seen in FIG. 14, thus increasing the effectiveness of treatments and further providing internal support which will be discussed in greater detail below. The Compression Layer 1020 may be secured between the Thermal Exchange Layer 1010 and a Cushion Layer 1030. Compression Layer 1020 may be secured by Hook Material 1023 releasably receiving complementary loop material on the Cushion Layer 1030 Surface 1033, and the loop material on the Compression Layer's 1020 Surface 1021 releasably receiving complementary Hook Material 1015 on the Thermal Exchange Layer 1010.

Figure 17A:
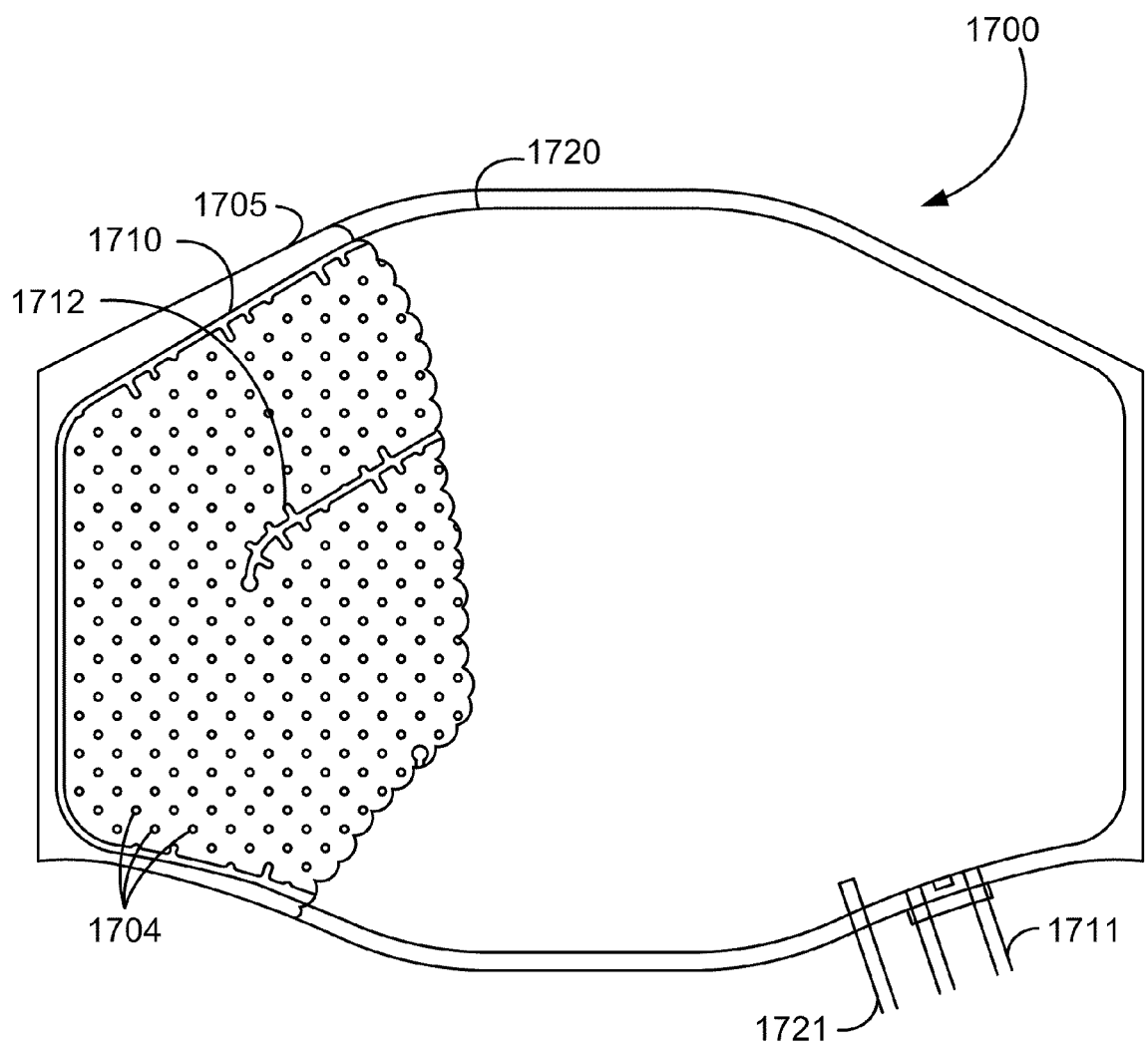
FIG. 17A shows a top plan cutaway view of an amalgamated bladder for use in a therapeutic spinal column brace system in accordance with an embodiment of the present invention.

In some embodiment, the Amalgamated Bladder 1700, seen in FIG. 17A, may include a Fluid Layer 1710 and a Pneumatic Layer 1720 in order to provide both thermal exchange and compression therapy. The Amalgamated Bladder 1700 may be adjacent to the therapy site, followed by the Cushion Layer 1030 and the Outer Layer 1040. The Amalgamated Bladder 1700 may include a First Membrane 1701, a second Membrane 1702 and a third Membrane 1703. These membranes may be welded together along a Common Outer Perimeter 1705, and/or at Intermittent Welds 1704, to define the Fluid Layer 1710 and the Pneumatic Layer 1720 on separate and adjacent planes. In some other embodiment, the Fluid Layer 1710 and Pneumatic Layer 1720 may be incorporated into the same plane and separated by divisional welds to define separate pneumatic and fluid chambers.

Figure 15:
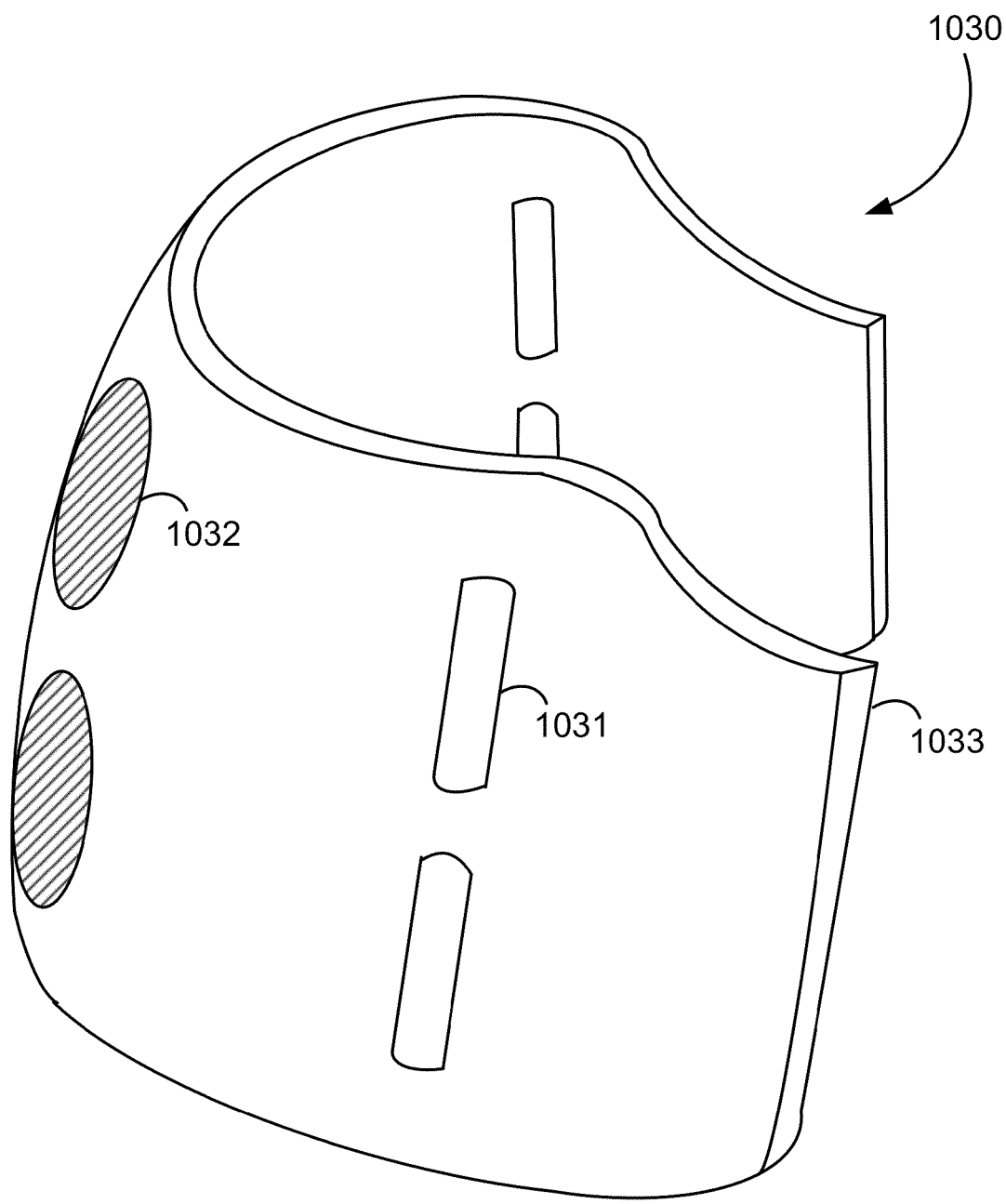
FIG. 15 shows an isometric view of a cushion layer for use in a therapeutic spinal column brace system in accordance with an embodiment of the present invention.

The Cushion Layer 1030, seen in FIG. 15, provides enhanced comfort to the therapy recipient and further ensures a proper fit of the Therapeutic Spinal Column Brace System 1000. The Cushion Layer 1030 may be secured between the Compression Layer 1020 and the Outer Layer 1040. Cushion Layer 1030 may be secured by Hook Material 1032 releasably receiving complementary Loop Material 1044 on the Outer Layer 1040.

Figure 16:
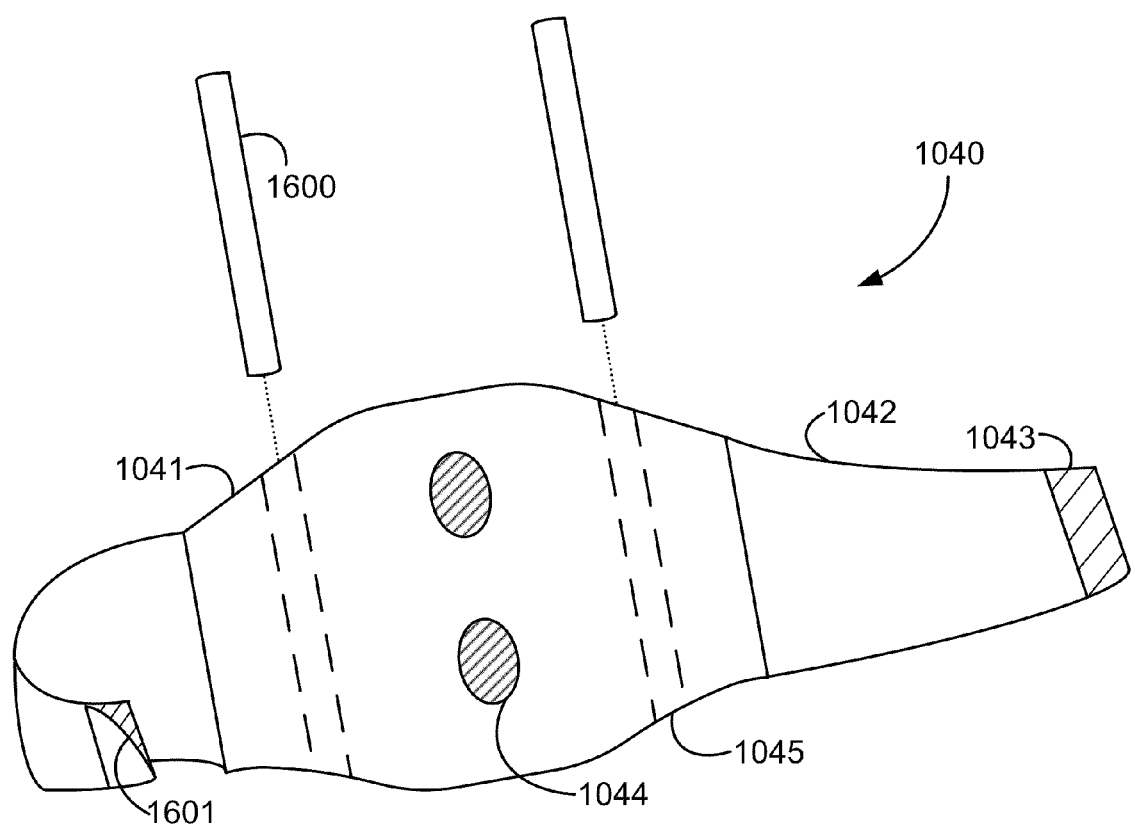
FIG. 16 shows an isometric view of an outer layer including a rigid support shell for use in a therapeutic spinal column brace system in accordance with an embodiment of the present invention.

The Outer Layer 1040, seen in FIG. 16, includes a Rigid Support Shell 1041, and provides the bulk of the support for the Therapeutic Spinal Column Brace System 1000. The Rigid Support Shell 1041 may be uniformly rigid, have gradients of rigidity for enhanced mobility, or may include one or more Support Braces 1045. The Outer Layer 1040 may include elastic or adjustable Straps 1042 for securing the entire Therapeutic Spinal Column Brace System 1000 to the therapy recipient. Hook Material 1043 configured to releasably receive complementary loop material may be used to secure the Straps around the therapy recipient. Additionally, by tightening the Straps 1042, additional compressive force may be applied to the therapy recipient.

The second spinal column brace with an interchangeable fluid therapy pad may be designed to provide greater flexibility and mobility for the wearer. Embodiments of this brace system may be seen at FIGS. 18A to 22. The increase in mobility and overall utility offered by these embodiments of the spinal column brace may be garnered with little reduction in overall spinal column support and contrast therapy exposure.

In some of these embodiments, the Interchangeable Lumbar Contrast Therapy Pad 1900 may include an integrated Therapy Bladder 1800 as well as a cushioning layer for comfort, support and compression. The Interchangeable Lumbar Contrast Therapy Pad 1900 may be reversibly detached to a Rigid Back Support System 2000. The Rigid Back Support System 2000 may also couple to a Rigid Frontal Support Panel 2100 to provide the support required to the wearers torso and spinal column. The Interchangeable Lumbar Contrast Therapy Pad 1900 may be designed to be replaceable by a standard cushion pad, thereby extending the functionality of this second spinal column brace. Likewise, by including a compact design for the Interchangeable Lumbar Contrast Therapy Pad 1900 with a shortened umbilical, the Interchangeable Lumbar Contrast Therapy Pad 1900 may be readily decoupled from the Contrast Therapy System 10, thereby increasing user mobility and reducing the need to remove the spinal column brace between contrast therapy sessions.

Fluid Circuit

Figure 2:
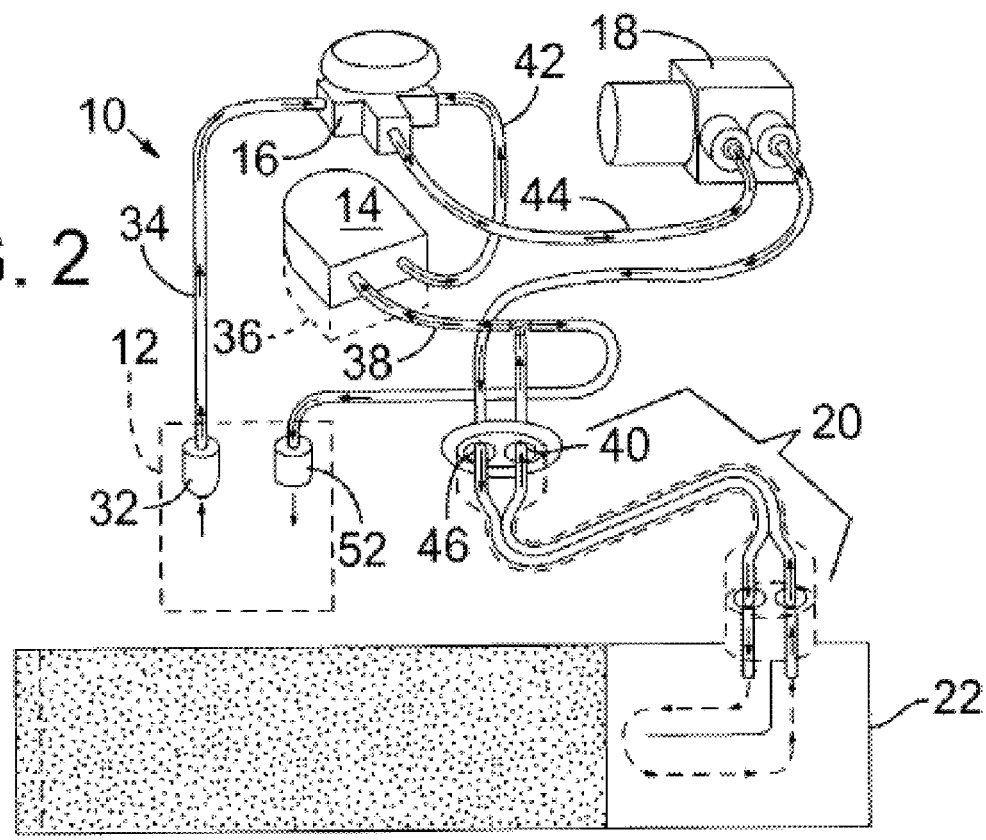
FIG. 2 is a schematic view of a fluid circuit for administering contrast therapy in accordance with an embodiment of the present invention.
Figure 3:
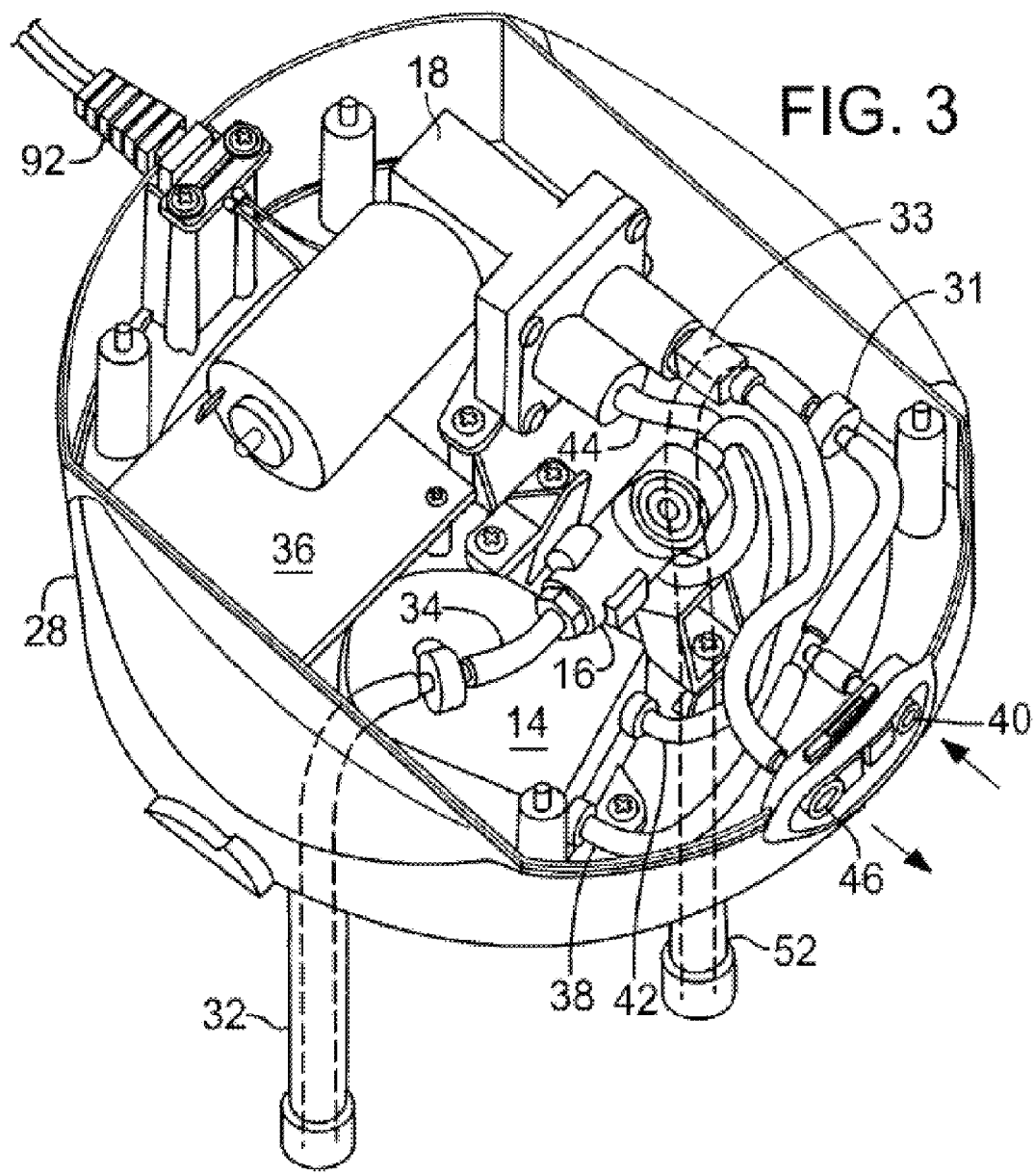
FIG. 3 is an isometric view of the fluid circuit of FIG. 2 housed within the lid portion of the contrast therapy system of FIG. 1.

FIG. 2 schematically shows a fluid circuit of the Therapeutic Spinal Column Brace System 1000 including a Contrast Therapy System 10, and FIG. 3 shows such a circuit housed by the Lid Unit 28 of a Portable Control Unit 30. As illustrated in FIGS. 2 and 3, the Therapeutic Spinal Column Brace System 1000 including a Contrast Therapy System 10 includes a Cold Reservoir 12, Hot Reservoir 14, Mixing Valve 16, Pump 18, Fluidic Coupling Assembly 20, and Therapy Pad 22 which may be a Thermal Exchange Layer 1010. As described in detail below, the Contrast Therapy System 10 is designed to control the temperature of a therapy fluid that circulates through the Therapy Pad 22, which includes the present Thermal Exchange Layer 1010. Mixing Valve 16 selectively combines fluid received from the cold and hot reservoirs and passes the combined fluid to the Therapy Pad 22 as a therapy fluid. The Mixing Valve 16 may control the temperature of the therapy fluid, changing between hot and cold temperatures in a short period of time.

Figure 1:
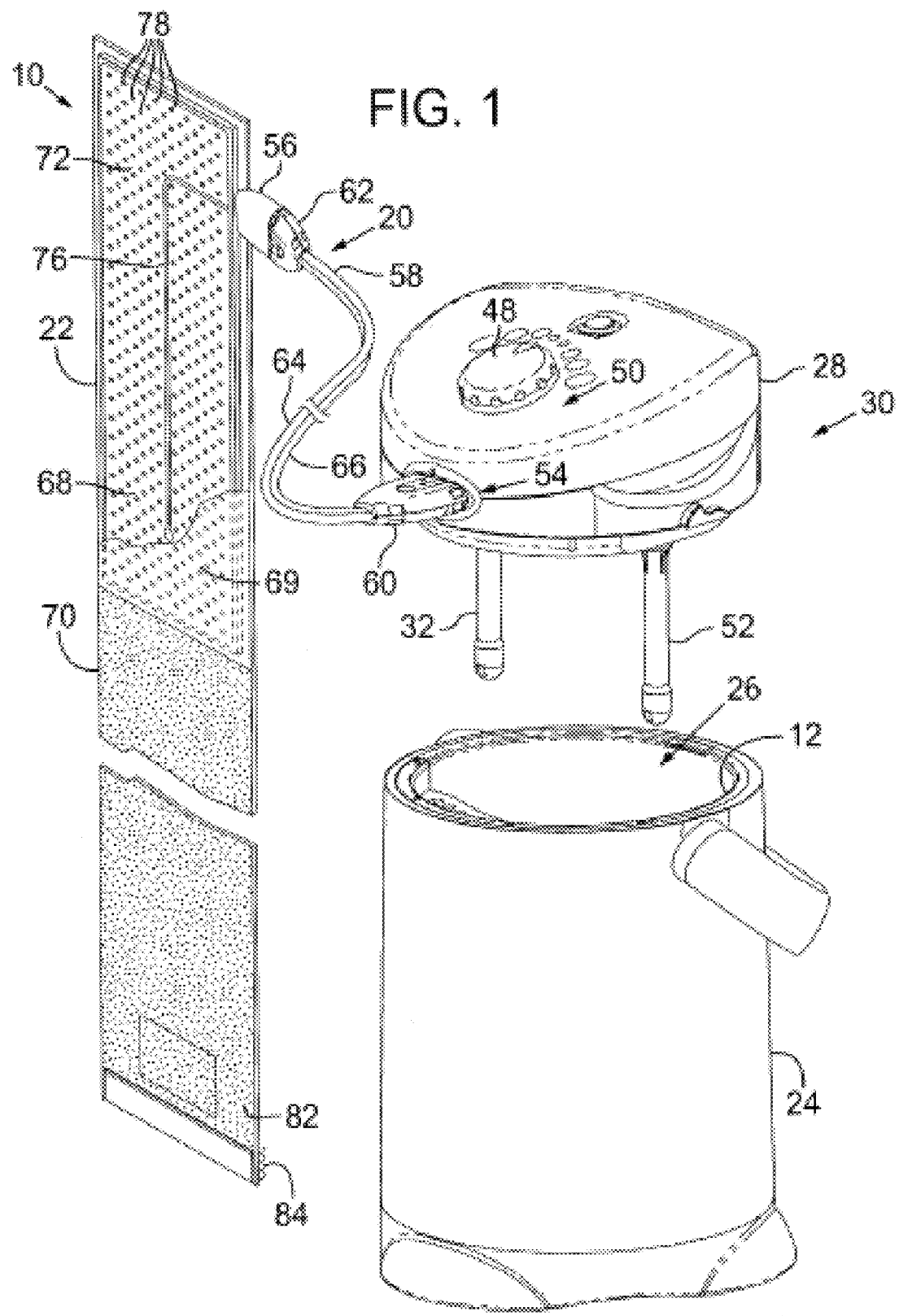
FIG. 1 is an isometric view of one embodiment of the contrast therapy system in accordance with the present invention.

Cold Reservoir 12 is designed to hold a relatively cold fluid, which may be passed to the Mixing Valve 16 and eventually to the Therapy Pad 22. As shown in FIG. 1, Cold Reservoir 12 may include the Container 24 with an Open End 26 suitable for receiving the Lid Unit 28. The Container 24 and the Lid Unit 28 may be components of the Portable Control Unit 30. The Cold Reservoir 12 may be dimensioned to hold virtually any volume of fluid, and is shown as a 4.2 Liter receptacle. Of course, smaller Cold Reservoirs 12 may be used, for example, when increased portability is desired, and larger Cold Reservoirs 12 may be used when, for example, increased capacity is desired.

The temperature of the Cold Reservoir 12 may be controlled by various mechanisms. In some embodiments, the Cold Reservoir 12 is adapted to receive ice that may melt in the Cold Reservoir 12, and thus decrease the temperature of the fluid in the Cold Reservoir 12. As shown in FIG. 1, Container 24 has a large Open End 26 that is suitable for easily receiving ice. In some embodiments, the Cold Reservoir 12 may include a cooler for cooling the fluid held in the Cold Reservoir 12. Such a cooler may include a compressor and a refrigerant, or similar cooling mechanism. It is within the scope of the invention, however, to use virtually any other suitable method for cooling the fluid held in Cold Reservoir 12. The Cold Reservoir 12 may include insulation to limit heat transfer between the fluid held by the Cold Reservoir 12 and the external environment.

The minimum temperature of the fluid in Cold Reservoir 12 is usually limited to approximately 32 to 45 degrees Fahrenheit, although such a limitation is not necessary. In particular, it has been found that a temperature of about 35 to 42 degrees Fahrenheit is an appropriate minimum temperature. Although water is usually used as the fluid, it is within the scope of the invention to use other suitable fluids. Such fluids may be selected for particular applications based on their specific heat, viscosity, freezing point, etc.

The Contrast Therapy System 10 may include an Intake 32 for drawing fluid from the Cold Reservoir 12. The drawn fluid may pass through a Fluid Path 34 between Cold Reservoir 12 and Mixing Valve 16, as is schematically shown in FIG. 1. Fluid Path 34, as well as other Fluid Paths described herein, may utilize ⅛ inch flexible tubing, or may alternatively implement another suitable fluid transport mechanism. For example, some or all of the Fluid Paths 34 may alternatively be defined by inflexible fluid conduits. The Fluid Path 34, or other fluid channels such as Intake 32, may include filters, flow restrictors, and/or check valves. Filters may help prevent flow blockages resulting from jammed ice or other substances, and check valves may be used to prevent backflow in the system. The rate of fluid flow may be at least partially controlled by flow restrictors.

Hot Reservoir 14 is designed to hold a relatively hot fluid, which may be passed to the Mixing Valve 16 and eventually to the Therapy Pad 22. Fluid in the Hot Reservoir 14 may be heated by a Heater 36, which may be positioned adjacent the Hot Reservoir 14, or may be incorporated into the Hot Reservoir 14. The Hot Reservoir 14 may be dimensioned to hold virtually any volume of fluid, and is shown dimensioned to hold a volume of approximately 20 to 30 cubic centimeters. It should be understood that the Hot Reservoir 14 may be smaller or larger, depending on the desired use and the other components of the contrast therapy system. Additionally, the Hot Reservoir 14 may be insulated to prevent heat loss from the Hot Reservoir 14 fluid to the external environment.

Heater 36 may be configured so as to achieve a suitable balance of power consumption and heat generation. It has been found that a heater of approximately 280 Watts is appropriate for heating a volume of approximately 20 to 30 cubic centimeters under normal conditions. It should be understood that more powerful and less powerful Heaters 36 may be used. Similarly, more than one heater or type of heater may be used.

The flow rate of fluid through the Hot Reservoir 14 may correspond to the temperature of treatment being applied, with greater flow rates occurring during hotter treatments. During some hot treatments, Heater 36 may have limited time to increase the temperature of the fluid because the fluid quickly passes through the Hot Reservoir 14, and thus, the heater should be powered so as to increase the temperature a desired amount within that constrained timeframe. However, the Heater 36 does not need to completely heat the fluid from a minimum temperature to a maximum temperature in such a timeframe, although it is within the scope of the invention to do so. The Hot Reservoir 14 receives fluid from the Therapy Pad 22, and when a hot treatment is being applied, the return fluid may already be partially heated, decreasing the magnitude of heating required from Heater 36. Thus, the net temperature of the fluid may incrementally increase as it repeatedly circulates through the Hot Reservoir 14. Nevertheless, a more powerful heater may increase the rate fluid increases temperature in the Hot Reservoir 14 and/or the maximum temperature of the fluid, thus decreasing the time required to change from a cold treatment to a hot treatment. The maximum temperature of the fluid in Hot Reservoir 14 is usually limited to approximately 100 to 110 degrees Fahrenheit, although such a limitation is not required. In particular, it has been found that a temperature of about 105 degrees Fahrenheit is appropriate.

As illustrated in FIGS. 2 and 3, Hot Reservoir 14 receives fluid via a Fluid Path 38 coming from a Bulkhead Input 40. As described below, Bulkhead Input 40 receives fluid returning from the Therapy Pad 22. The returning fluid may be directed so that fluid may go to at least one of the Hot Reservoir 14, via Fluid Path 38, and the Cold Reservoir 12, via a Return 142. In some embodiments, the Hot Reservoir 14 may be housed within Lid Unit 28, which may be securely fit to Open End 26 of Container 24. Heater 36 may be controlled by an internal control system, external control system, or no control system whatsoever. If present, a control system may regulate the maximum temperature of fluid in the Hot Reservoir 14, for example. Such a control system may also be designed to maximize heating efficiency to limit energy requirements.

Contrast Therapy System 10 may include a Power Supply, such as 92 of FIG. 3, for providing power to various components of the system, such as a heater, cooler, pump, thermostat, display, etc. In some embodiments, the power supply may provide alternating current, while in other embodiments, the power supply may provide direct current. Some embodiments may be configured to operate with either AC or DC power. For example, the contrast therapy system may include a DC heater and pump designed to draw power from either a battery or an electrical outlet via an AC/DC converter. Batteries used to power the contrast therapy system may be externally connected to the system, and/or housed within the system. The contrast therapy system may be powered from alternative power sources as well.

Mixing Valve

Spinal Column Brace Including Contrast Therapy System 10 includes the Mixing Valve 16 for receiving a selected ratio of the hot and cold fluids from the Hot Reservoir 14 and Cold Reservoir 12. The Mixing Valve 16 is operable to deliver a therapy fluid with a therapy temperature that is determined by the selected ratio. In other words, Mixing Valve 16 may adjustably control the amount of hot fluid from the Hot Reservoir 14 and the amount of cold fluid from the Cold Reservoir 12 that mix together. The ratio may be 100% hot fluid from the Hot Reservoir 14, in which case the resulting therapy fluid would have a therapy temperature substantially equal to the temperature of fluid leaving the Hot Reservoir 14 (maximum temperature). The ratio may alternatively be 100% cold fluid from the Cold Reservoir 12, in which case the resulting therapy fluid would have a therapy temperature substantially equal to the temperature of fluid leaving the Cold Reservoir 12 (minimum temperature). Any temperature in between the maximum and minimum temperature may be achieved by adjusting the ratio.

The mixing valve is linked to the Cold Reservoir 12 and the Hot Reservoir 14 by respective Fluid Paths 34 and 42. In some embodiments, one or both of Fluid Paths 34 and 42 may include a pump, although no pump is required. The Mixing Valve 16 outputs therapy fluid to a Fluid Path 44 that leads to the Bulkhead Output 46, and eventually to the Therapy Pad 22. A Pump 18 may be included between the Mixing Valve 16 and the Therapy Pad 22, as shown in FIGS. 2 and 3 and described below. As with the other Fluid Paths of the contrast therapy system, these Fluid Paths may include flow restrictors, check valves, filters, over-pressure switches, and/or other components. For example, Check Valve 31 and Over Pressure Switch 33 are illustrated in FIG. 3. The flow paths may include flexible rubber tubing that is approximately ⅛ inch in diameter.

As shown in FIG. 1, the Mixing Valve 16 may be controlled by a Dial 48 that adjusts the ratio of hot and cold fluids delivered from the mixing valve. The Dial 48 may be associated with Indicia 50 that indicate a relative magnitude of a desired therapy temperature. For example, Indicia 50 may include a series of icons representing relative temperatures. A large red dot may represent the hottest therapy temperature, with red dots decreasing in size representing decreasing temperatures. Similarly, a large blue dot may represent the coldest therapy temperature, with blue dots decreasing in size representing increasing temperatures. The Dial 48 positioned to point to the large red dot may correspond to a mixing valve position that yields a ratio of 100% hot fluid. As the Dial 48 is turned through the progressively smaller red dots, and then through the progressively larger blue dots, the ratio may yield a therapy fluid with a continually increasing percentage of cold fluid.

In some embodiments, the Contrast Therapy System 10 may include a thermostat that automatically selects the ratio of hot and cold fluids delivered from the Mixing Valve 16. For example, the thermostat may be designed to receive manual input of a desired therapy temperature, and adjust the mixing valve to yield a therapy fluid with that temperature. Accordingly, the thermostat may include a temperature measuring device (not shown), such as a thermistor, thermometer, thermocouple, etc. The temperature measuring device may monitor the temperature of the therapy fluid as the thermostat adjusts the mixing valve to yield the desired therapy temperature. The temperature measuring device may cooperate with a temperature display to present the temperature of the therapy fluid. The thermostat may be programmable to automatically change the therapy temperature at a desired time or event by adjusting the ratio of hot and cold fluids delivered from the mixing valve. For example, the thermostat may be programmed to provide alternating hot therapies that last for five minutes at 105 degrees Fahrenheit and cold therapies that last for 5 minutes at 40 degrees Fahrenheit. It should be understood that the thermostat may be programmed for therapies of different durations and/or temperatures.

As shown in FIGS. 2 and 3, the Contrast Therapy System 10 may include a Pump 18 for circulating fluid through the system. As illustrated, the Pump 18 interposes the Mixing Valve 16 and the Bulkhead Output 46, although the Pump 18 may be positioned elsewhere. Similarly, more than one pump may be utilized. As is shown, the Pump 18 may be integrated into the Lid Unit 24 of the Portable Control Unit 30. The Pump 18 may be powered according to the desired application, and a 4 Watt pump capable of pumping 300 cubic centimeters of fluid per minute has been found to be suitable. The Pump 18 may be a reciprocating pump, a rotary pump, or virtually any other suitable pump.

In some embodiments, the Pump 18 may be configured to pulse the therapy fluid through the Therapy Pad 22. Such a pulsing action may be translated into a therapeutic massage via the Therapy Pad 22. As the pulsing fluid circulates through the Therapy Pad 22, the Therapy Pad 22 may vibrate. Pumps designed to pulse fluid may be further enabled to adjust the relative magnitude of the pulsing to correspond to different intensities of therapeutic massages. The relative intensity may be automatically, or manually, coordinated to correspond to a particular temperature of treatment. For example, a vigorous massage may be applied during a hot treatment while a milder massage is applied during a subsequent cold treatment.

Fluidic Coupling Assembly

Figure 4:
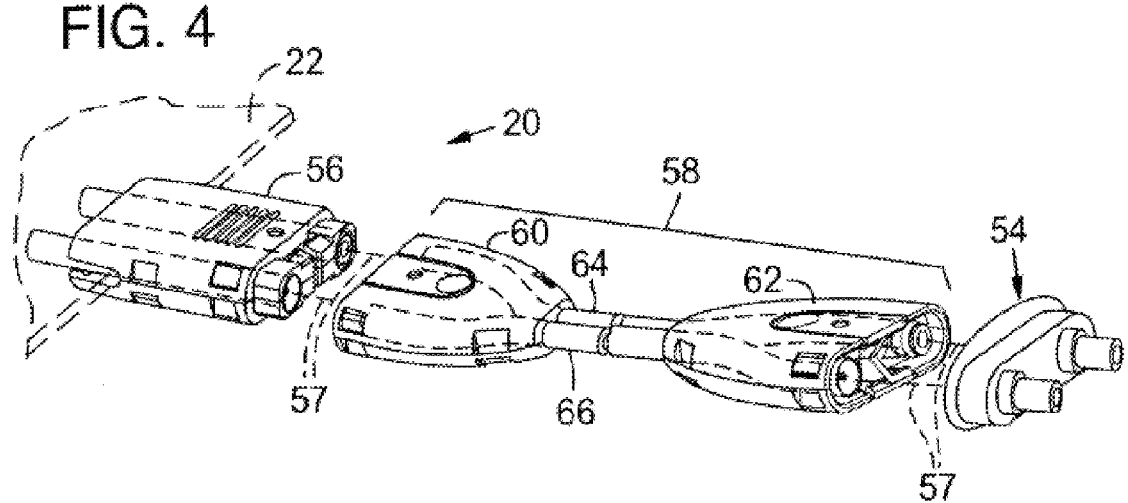
FIG. 4 is an isometric view of a fluidic coupling assembly in accordance with an embodiment of the present invention.

Therapeutic Spinal Column Brace System 1000 including Contrast Therapy System 10 may include the Fluidic Coupling Assembly 20 to selectively couple and decouple the Portable Control Unit 30 and the Therapy Pad 22 or, in the present invention, the Thermal Exchange Layer 1010. As shown in FIG. 4, the Fluidic Coupling Assembly 20 usually includes a Bulkhead 54, which is in fluid communication with the Mixing Valve 16, a Bladder Connector 1012, or Wrap Connector 56, in fluid communication with the Thermal Exchange Bladder 1200, and a Reversible Tubing Assembly 58 for linking the Bulkhead 54 to the Bladder Connector 1012. The Reversible Tubing Assembly 58 includes a First Tube-Set Connector 60 and a Second Tube-Set Connector 62 that are functionally equivalent to one another. Of course the First Tube-Set Connector 60 and the Second Tube-Set Connector 62 may be designed to differ from one another to limit connectivity as desired. First Tube-Set Connector 60 and Second Tube-Set Connector 62 are linked by Fluid Paths 64 and 66.

Bulkhead 54, First Tube-Set Connector 60, Second Tube-Set Connector 62, and Bladder Connector 1012 each include one male valve and one female valve, which are configured to mate with a corresponding female and male valve, for example, as shown by dotted lines 400 in FIG. 4. The Bulkhead 54 and the Bladder Connector 1012 are each configured to releasably receive either the First Tube-Set Connector 60 or the Second Tube-Set Connector 62. Therefore, Tubing Assembly 58 is completely reversible. For example, the Bulkhead 54 and the First Tube-Set Connector 60 may be coupled so that the Bulkhead's 54 male valve mates with the First Tube-Set Connector's 60 female valve, and the Bulkhead's 54 female valve mates with the First Tube-Set Connector's 60 male valve. Likewise, the Bladder Connector 1012 and the Second Tube-Set Connector 62 may be coupled so that the Bladder Connector's 1012 male valve mates with the Second Tube-Set Connector's 62 female valve, and the Bladder Connector's 1012 female valve mates with the Second Tube-Set Connector's 62 male valve. Because the tubing assembly is reversible, the above described connection may be reversed. For example, if the First Tube-Set Connector 60 is connected to the Bulkhead 54, the Second Tube-Set Connector 62 is available for connection to the Bladder Connector 1012, but if the Second Tube-Set Connector 62 is connected to the Bulkhead 54, the First Tube-Set Connector 60 is available for connection to the Bladder Connector 1012. In either case, such arrangements permit fluid to flow from the Portable Control Unit 30 to the Thermal Exchange Bladder 68, 1200, and then return back to the Portable Control Unit 30.

The male and female valves of each of the above described components are equally spaced from one another. Therefore, male and female valves from one component may align with female and male valves from a corresponding component. Furthermore, Bulkhead 54 is complementarily configured relative to both the First and Second Tube-Set Connectors 60, 62 to facilitate securing either the First Tube-Set Connector 60 or the Second Tube-Set Connector 62 to the Bulkhead 54. Similarly, either the First Tube-Set Connector 60 or the Second Tube-Set Connector 62 may be secured to the Bladder Connector 1012. The male and female valves are designed to prevent fluid flow unless they are mated with one another, thus limiting leakage when disconnecting the Reversible Tubing Assembly 58 from the Portable Control Unit 30 and/or the Thermal Exchange Layer 1010.

The configuration of the Fluidic Coupling Assembly 20 facilitates easy connection and disconnection of a plurality of Portable Control Units 30, Tubing Assemblies 58, Thermal Exchange Layers 1010 and/or other thermal Therapy Pads 22. For example, the same Portable Control Unit 30 may be used with a variety of different Therapy Pads 22, which may be individually configured to treat different areas of a recipient's body. Similarly, Thermal Exchange Layer 1010 incorporated in a Therapeutic Spinal Column Brace System 1000 may be used with a variety of different Portable Control Units 30, for example, when a recipient moves from one therapy location to another. The Fluidic Coupling Assembly 20 facilitates quick and easy coupling and decoupling, and the leak reducing male and female valves help limit spillage during such coupling and decoupling.

Therapy Pad

Figure 5:
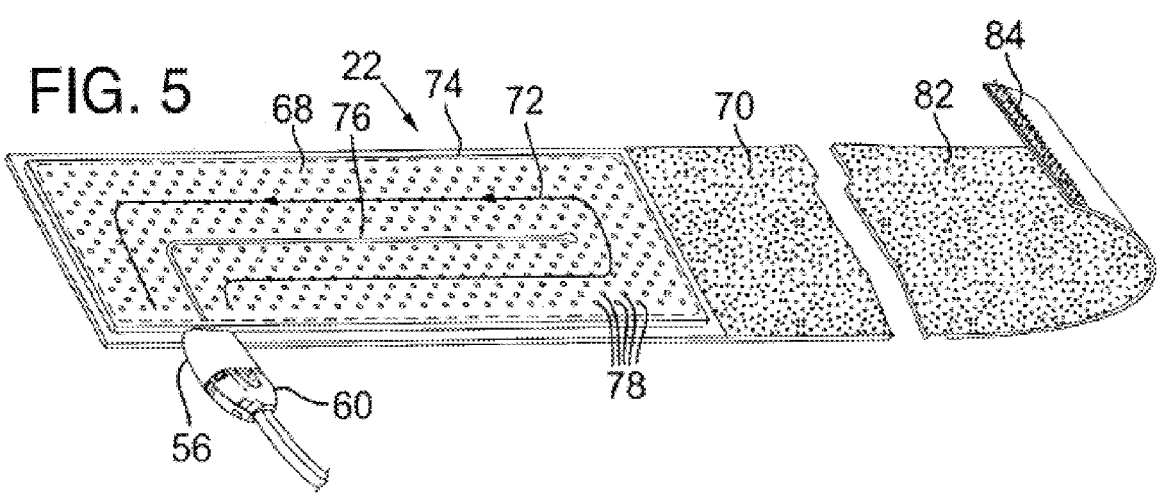
FIG. 5 is an isometric view of a contrast therapy pad in accordance with an embodiment of the present invention.

FIG. 5 shows Therapy Pad 22 apart from the remainder of the contrast therapy system. As described above, the Therapy Pad 22 may be easily coupled and decoupled from the Reversible Tubing Assembly 58, which allows various different Therapy Pads 22 to be used with the same control unit. Each Therapy Pad 22 is designed to receive therapy fluid from the mixing valve, such as through the fluidic coupling assembly, and return the therapy fluid to at least one of the hot reservoir and the cold reservoir (as shown schematically in FIG. 2). The Therapy Pad 22 returns fluid to the control unit, and the returned fluid may be recirculated. Depending on the type of therapy being applied, returned fluid may be heated and/or cooled at the control unit. The contrast therapy system may include a return valve that selectively directs return fluid to the hot reservoir and/or the cold reservoir, or the return fluid may be allowed to naturally flow to the lower pressure region.

Figure 6:
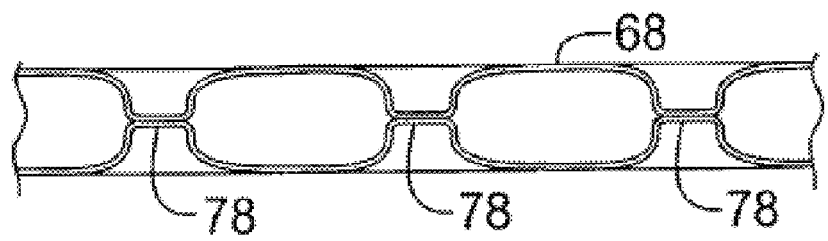
FIG. 6 is a cross-sectional view of a portion of the contrast therapy pad of FIG. 5.

In some embodiments, the Therapy Pad 22 includes an active Thermal Exchange Bladder 68 and an Elastic Wrap 70 that is connected to the Thermal Exchange Bladder 68. The Thermal Exchange Bladder 68 may include a flexible membrane of opposing faces that are welded together to define a channel system for directing the flow of therapy fluid along a desired Fluid Path 72 within the Thermal Exchange Bladder 68. For example, the faces are usually welded along a common Outer Perimeter 74, sealing the faces together. A division weld 76 may direct fluid through a substantial portion of the pad before returning to the control unit. The Thermal Exchange Bladder 68 may also include a plurality of Intermittent Welds 78, that limit inflation of the bladder, as shown in FIG. 6, which is a cross-sectional view of a portion of the exchange bladder.

The Thermal Exchange Bladder 68 facilitates thermal exchange between a therapy site and the therapy fluid. For example, when a cold therapy is administered, heat from a recipient's body may heat the therapy fluid, which in turn cools the therapy site. Similarly, when a hot therapy is administered, the therapy fluid may transfer heat to the therapy site. The therapy may be enhanced by moistening the bladder to provide a moist therapy. Furthermore, the fluid may also be pulsed through the bladder, adding a therapeutic massage aspect to the treatment.

In the illustrated embodiment, Therapy Pad 22 is dimensioned to hold approximately 26 cubic centimeters of fluid. However, the volume of the Therapy Pad 22 may be controlled by changing the size of the Therapy Pad 22, and/or the amount of inflation the intermittent welds allow. Furthermore, the Therapy Pad 22 may be constructed from an at least partially elastic material, such as urethane, which may permit the volume to change in response to the pressure of fluid within the bladder. In some embodiments, the bladder may include a less elastic material that helps prevent stretching, such as a vinyl/urethane blend.

As shown in FIG. 5, fluid may enter the bladder at Wrap Connector 56, flow around the division weld and the Intermittent Welds 78, and leave the bladder at the Wrap Connector 56. It is within the scope of the invention to reconfigure the bladder to accommodate different flow paths. For example, the division weld, or plural division welds, may be used to direct the fluid through a series of switchbacks before returning to the output of the Wrap Connector 56. Small breaks may be included in the division weld to permit alternative flow paths if a primary flow path is blocked.

Elastic Wrap 70 is shown connected to the Thermal Exchange Bladder 68. The Elastic Wrap 70 may be configured to adjustably wrap around the Thermal Exchange Bladder 68 and compress the Thermal Exchange Bladder 68 around a therapy site. Compression helps induce contact of the bladder with the therapy site, which may promote efficient and even thermal transfer. Furthermore, the wrap is a compressive element in and of itself. When used in conjunction with the bladder, it keeps the bladder in contact with the therapy site, and it may also help reduce swelling through its own inherent compressibility. The wrap is continuously adjustable, meaning it may be repeatedly tightened and loosened to various levels of compression, as shown in FIG. 7. The wrap may be used in tandem with the bladder to wrap a therapy site in a variety of ways, thus providing extreme flexibility in the types of treatments that may be administered to a wide range of different therapy sites.

Figure 7A:
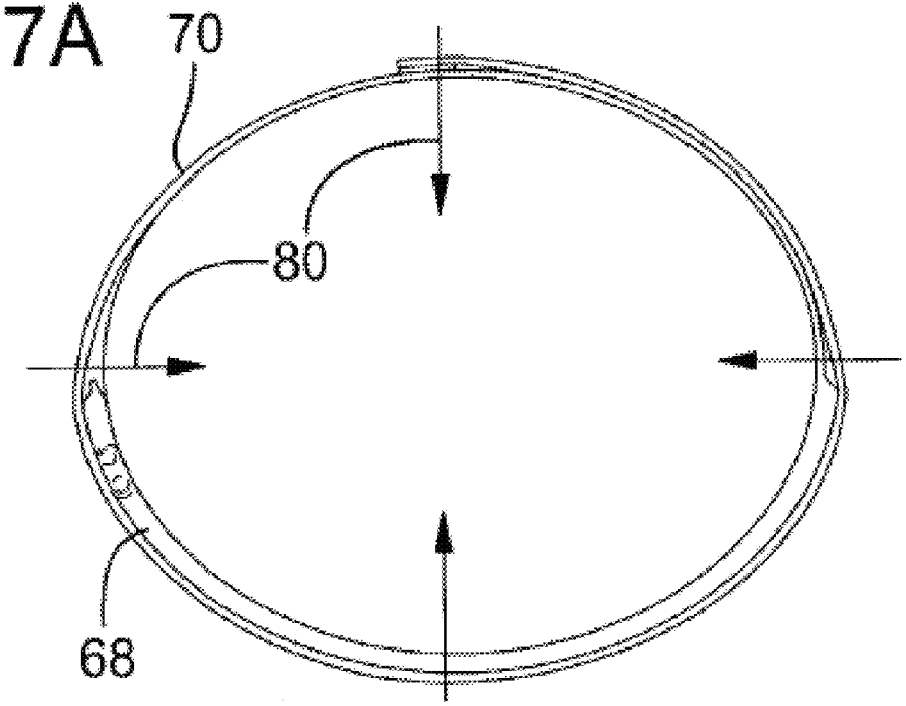
FIG. 7A is a cross-sectional view of the therapy pad of FIG. 7 wrapped around the therapy recipient.

Wrap 70 is elastic; it may be stretched and naturally return to an unstretched disposition. When stretched, the wrap is at an increased tension, which may be used to compress a Therapy Pad 22 around a therapy site, as shown in FIG. 7A. Force vectors 80 schematically represent the compressive force resulting from the wrap. The magnitude of the compressive force may be selected by adjusting the amount the wrap is stretched. As the wrap is increasingly stretched around a therapy site, the compressive force the wrap applies increases. Similarly, the wrap may be loosened, decreasing the magnitude of the compressive force. The amount of elasticity a particular wrap has may be selected according to a desired application, or range of applications. In some embodiments, the wraps are designed to stretch to approximately 150%-200% of their unstretched length, however less elastic and more Elastic Wraps 70 may be used. The wraps may be variously sized, and are usually at least as long as their corresponding bladder when unstretched. As illustrated in FIG. 5, the unstretched wrap is six times as long (54 inches) as the bladder (18 inches). Because of the elastic configuration of the wrap, wrapping techniques known to physical therapists, physical trainers, and sports physicians may be used in conjunction with the Therapy Pad 22 to achieve a wide variety of therapeutic benefits.

As shown in FIG. 5, Elastic Wrap 70 is permanently connected to Thermal Exchange Bladder 68. The wrap may be connected by stitching, an adhesive, and/or another suitable fastener. In some embodiments, the bladder is connected to the wrap via an optional mesh envelope, shown in dashed lines at 69. In such embodiments, the envelope may be permanently connected to the wrap, and the bladder may be selectively positioned within the mesh envelope. The mesh envelope may include a fastening face configured to selectively fasten with a complementary fastener of the wrap. The wrap may alternatively be removably connected to the bladder, such as by hook and loop connectors. By permanently connecting the wrap to the bladder, such as by stitching or configuring an envelope to securely hold the bladder relative to the wrap, the wrap and the bladder may cooperate to provide a compressive force, as described herein. Furthermore, the combination has proven to be much easier to apply than separated Therapy Pads and wraps, and thus is more versatile.

The wrap usually includes a surface of loops 82 that are adapted to detachably receive complementary hooks 84. The hooks and loops are positioned, so that the hooks may engage the loops when the wrap is wrapped around a therapy site, as shown in FIGS. 7 and 7A. The wrap may be adjusted to a desired tension and a corresponding level of compressive force that may be fixed by engaging the hooks and the loops together. The hooks and loops may subsequently be disengaged, so that the tension may be adjusted, for instance, and reengaged at will. In some embodiments, a wrap lock may alternatively be used to secure the wrap.

In some embodiments, the Therapy Pads 22 may be constructed with disposable materials. For example, pads configured for a single use may be constructed from disposable materials, which are usually less expensive than reusable materials. Disposable Therapy Pads 22 may be particularly useful in emergency, trauma, or post surgery situations, in which a therapy recipient may bleed onto the Therapy Pad 22. The ability to control the temperature of the Therapy Pad 22, either reusable or disposable, may increase the pad's effectiveness as a wound dressing. Disposable materials may include less resilient versions of reusable materials and/or completely different materials. In some embodiments, disposable materials may include apertured, breathable, elastomeric and/or embossed films, as well as nonwoven laminates. Wraps may alternatively be configured to be washable, such as by a laundry machine, and therefore may be sanitarily reused.

The Thermal Exchange Bladder 68 may be sized and shaped according to a particular range of applications. For example, a 6 inch by 18 inch bladder (as shown at 22 in FIG. 5) may be useful in treating backs, legs, arms, shoulders, and other therapy sites. Although the versatile configuration of Therapy Pad 22 may be used for virtually any therapy site, other Therapy Pads 22 may be configured to even better accommodate particular therapy sites. For example, a 2 inch by 18 inch bladder 86, as shown in FIG. 8, may be particularly useful for treating smaller therapy sites, such as hands, wrists, feet, ankles, etc. Similarly, a shoulder Therapy Pad 22 may be designed to intimately engage a shoulder therapy site, thus providing comfortable and improved treatment. A jaw Therapy Pad 22, which is useful in treating the facial area, may be designed to comfortably wrap around a head, while positioning a bladder in contact with at least one side of a jaw. It should be understood that the above Therapy Pads are provided as examples, and other Therapy Pads may also be used. Furthermore, each Therapy Pad 22 may include a suitable Elastic Wrap 70 and/or other fastening mechanism.

The therapy system may be used to treat a wide range of conditions, including injured muscles, bones, joints, tendons, ligaments, etc. Furthermore, other conditions may be treated, such as mastitis or breasts that are sore from menstruation. The therapy system may also be used as a preventative remedy, for example the therapy system may be used during childbirth to help alleviate discomfort during labor as well as help minimize resulting soreness and/or discomfort. For example, providing a cold treatment to a recipient's back during childbirth may help cool the recipient, thus alleviating immediate discomfort, as well as subsequent soreness.

Method of Administering Contrast of Thermal Therapy

FIG. 9 shows, generally at 900, a method of administering contrast therapy to a therapy recipient. Method 900 includes, at 901, providing a volume of a relatively hot fluid. As explained above, a fluid may be received by a hot reservoir, where it may be heated by a heater. The relatively hot fluid may be virtually any temperature, with temperatures of approximately 100 to 105 degrees Fahrenheit being suitable for many applications. The method further includes, at 902, providing a volume of a relatively cold fluid. Fluid may be received by a cold reservoir, where it may be cooled. In some embodiments, ice slurry is used to cool fluid passing through the cold reservoir, and in some embodiments a cooler is used. The cold fluid may be virtually any temperature (cooler than the hot fluid), with temperatures of approximately 32 to 45 degrees Fahrenheit being suitable for many applications.

At 903, the method includes selecting relative amounts of the hot and cold fluids to mix as a therapy fluid with a desired initial therapy temperature. A mixture of hot and cold fluids with a specific ratio may be selected with a mixing valve, or similar mechanism, that is configured to receive the hot and cold fluids, and pass the mixture of the hot and cold fluids as a therapy fluid. The ratio of hot to cold fluid in the therapy fluid may range from 100% hot fluid to 100% cold fluid, as well as any intermediate ratio. The temperature of the therapy fluid corresponds to the ratio of hot and cold fluids mixed, with greater percentages of hot fluid resulting in higher temperatures, and greater percentages of cold fluid resulting in cooler temperatures. The therapy fluid's maximum temperature is approximately the temperature of the hot fluid, and is achieved by selecting a ratio of all hot fluid and no cold fluid. Similarly, the therapy fluid's minimum temperature is approximately the temperature of the cold fluid, and is achieved by selecting a ratio of all cold fluid and no hot fluid.

As shown at 904, the method further includes circulating the therapy fluid with the initial therapy temperature through a Therapy Pad 22, which includes the Thermal Exchange Layer 1010 of the present invention. The therapy fluid may be circulated in a pulsing stream, so as to impart a vibration that is useful in providing a therapeutic massage. Of course, the flow may instead be smooth. At 905, the method includes applying the Therapy Pad 22, here a Thermal Exchange Layer 1010, to the therapy recipient. This may be performed by donning the Therapeutic Spinal Column Brace System 1000. The Therapeutic Spinal Column Brace System 1000 additionally supplies spinal column support, and therapy site compression, which may aid in the overall therapy. The temperature of the therapy fluid may be translated through the Therapy Pad 22, here a Thermal Exchange Layer 1010, to the therapy recipient. For example, if the initial temperature of the therapy fluid is relatively hot, for instance 105 degrees Fahrenheit, the Thermal Exchange Layer 1010 may be used to heat a therapy site on the therapy recipient. Similarly, a therapy fluid with a relatively cold therapy temperature, such as 40 degrees Fahrenheit, may be used to cool a therapy site.

The method further includes, at 905, returning the therapy fluid to at least one of the volume of hot fluid and the volume of cold fluid. Returning the therapy fluid to either or both of the volumes of hot and cold fluids allows the therapy fluid to be recycled. The returned therapy fluid may then be heated and/or cooled, and eventually may be recirculated to the Therapy Pad 22, here the Thermal Exchange Layer 1010. In this manner, a limited volume of fluid in a system may be used to provide an ongoing therapy. The fluid may be repeatedly heated and/or cooled, and thus the character of the treatment may be continually changed.

As shown at 906, the method may also include selecting relative amounts of the hot and cold fluids to mix as a therapy fluid with a desired contrast therapy temperature different than the initial therapy temperature. By changing the relative amounts of hot and cold fluids, the resulting temperature of the therapy fluid may be changed, which changes the therapy received by the therapy recipient. It is within the scope of the invention to make such temperature changes quickly, such as in under a minute, which may result in an average temperature change greater than 1 degree Fahrenheit per second. At 907, the method may further include circulating the therapy fluid with the contrast therapy temperature through the Therapy Pad 22, here the Thermal Exchange Layer 1010. Circulating the therapy fluid with the contrast therapy temperature allows the therapy recipient to experience a cold treatment immediately after a hot treatment or a hot treatment immediately after a cold treatment. It should be understood that the period of change between respective treatments is ideally very small, such as less than one minute. This process may be repeated one or more times, and each time the relative amounts of hot and cold fluids may be selected to result in a desired therapy temperature.

Therapeutic Spinal Column Brace System Assemblies

I. First Embodiment

Figure 10:
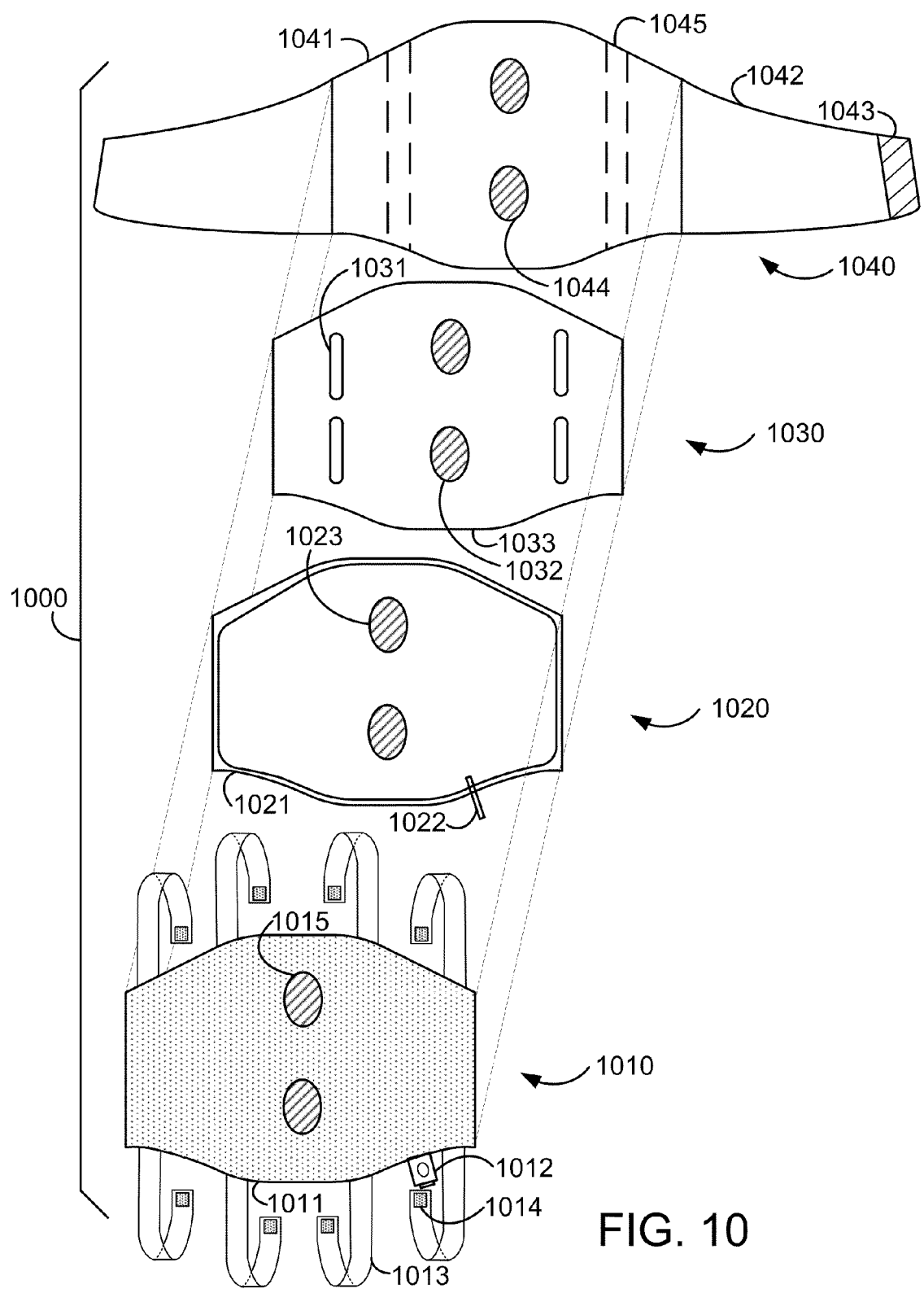
FIG. 10 shows an isometric view of a therapeutic spinal column brace system in accordance with an embodiment of the present invention.

FIG. 10 shows a view of the first embodiment of the Therapeutic Spinal Column Brace System 1000. As compared to later embodiments for the spinal column brace, this embodiment may include greater amounts of support and coverage. Likewise, the system may be marginally larger and afford the wearer a lesser degree of mobility as compared to other brace designs. As such, this embodiment of the Therapeutic Spinal Column Brace System 1000 may be of particular use in post operational situations where mobility of the wearer is not of paramount concern, but rather support and healing are considered paramount.

This Therapeutic Spinal Column Brace System 1000 is capable of imparting great levels of support to a therapy recipient, and provides a medium for the Contrast Therapy System 10 across a wide area of the wearer's torso (including much of the lumbar and middle back). The Therapeutic Spinal Column Brace System 1000 includes multiple layers that are secured around the torso of the therapy recipient. These layers include, from therapy site outward, the Thermal Exchange Layer 1010, a Compression Layer 1020, a Cushion Layer 1030 and an Outer Layer 1040. Alternatively, in some embodiment, an Amalgamated Bladder 1700 may be utilized to replace the Thermal Exchange Layer 1010 and Compression Layer 1020. The Thermal Exchange Layer 1010, or in some embodiment the Amalgamated Bladder 1700, may be coupled to the contrast therapy system Portable Unit 30 through a Fluidic Coupling Assembly 20.

The Thermal Exchange Layer 1010 has Adjustable Elastic Straps 1013 that encircle the Compression Layer 1020, the Cushion Layer 1030 and the Outer Layer 1040, thereby securing the Therapeutic Spinal Column Brace System 1000 together. The Adjustable Elastic Straps 1013 are designed to stretch to approximately 150%-200% of their unstretched length, however less elastic and more elastic straps may be used. A surface of Hooks 1014 is adapted to detachably receive complementary loops on the surface of Adjustable Elastic Straps 1013. The Hooks 1014 and loops are positioned so that the Hooks 1014 may engage the loops when the Thermal Exchange Layer 1010 is coupled with the Compression Layer 1020, the Cushion Layer 1030 and the Outer Layer 1040. The Therapeutic Spinal Column Brace System 1000 may be adjusted to a desired tension to ensure solid coupling of all layers and may be fixed by engaging the Hooks 1014 and the loops together. The Hooks 1014 and the loops may subsequently be disengaged, so that the tension may be adjusted, for instance, and reengaged at will. In some embodiments, a wrap lock, belt buckles, lacing or any other acceptable method may alternatively be used to secure the Adjustable Elastic Straps 1013 around the multiple layers of the Therapeutic Spinal Column Brace System 1000.

Figure 11A:
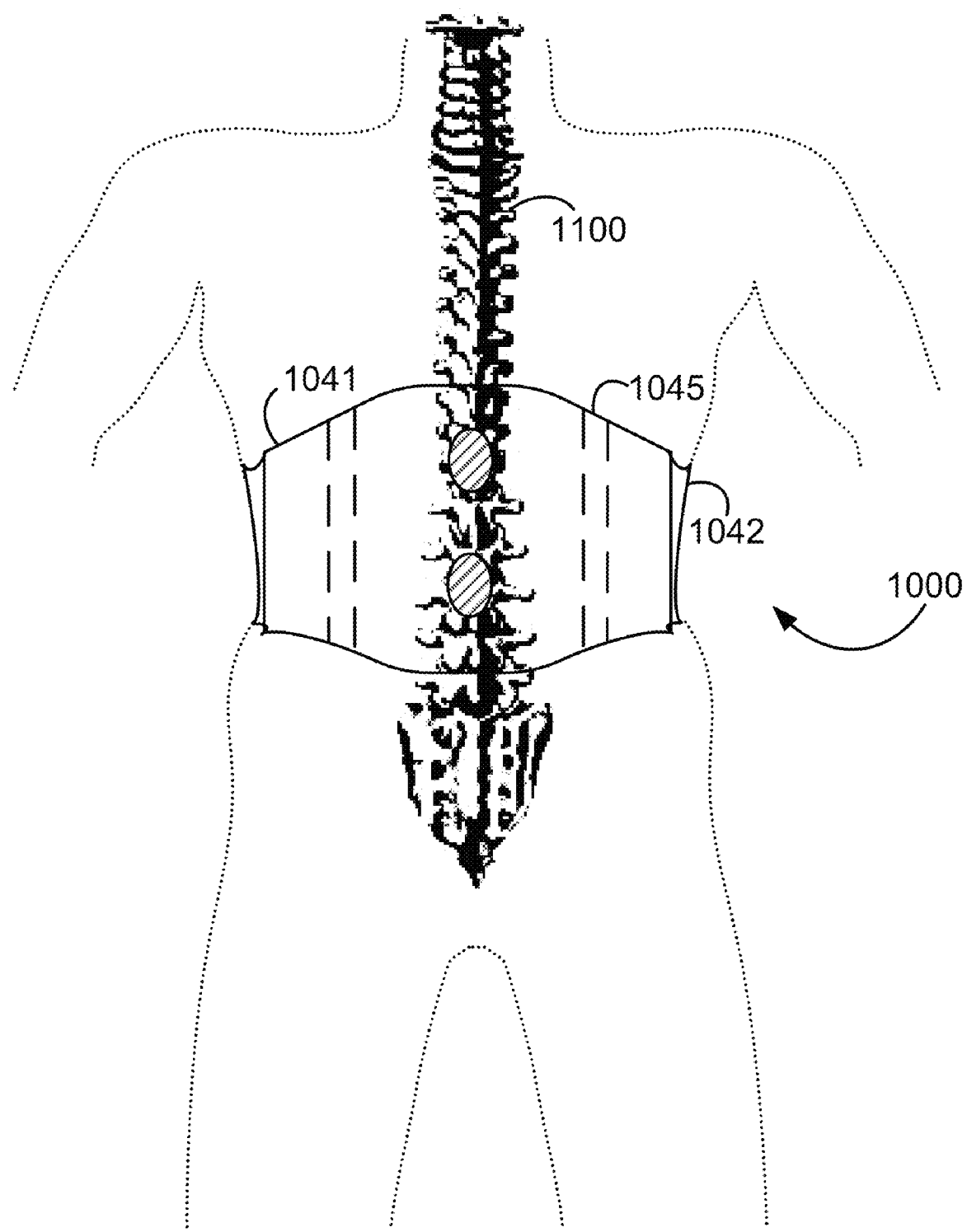
FIG. 11A shows an isometric view of a therapeutic spinal column brace system secured to the therapy site of a therapy recipient in accordance with an embodiment of the present invention.

FIG. 11A shows a view of the Therapeutic Spinal Column Brace System 1000 secured to the therapy site of a therapy recipient in accordance with an embodiment of the present invention. The Therapeutic Spinal Column Brace System 1000 encircles the recipient's torso with the center of the Outer Layer 1040 centered on the recipient's spine. The base of the Therapeutic Spinal Column Brace System 1000 should rest above the sacral vertebrae and extend up along the lumbar vertebrae. Support Braces 1045 are integrated into the Rigid Support Shell 1041 of the Outer Layer 1040 of the Therapeutic Spinal Column Brace System 1000. The Support Braces 1045 typically extend along the spinal axis to provide optimal support, however other Support Brace 1045 configurations may be used.

Figure 11B:
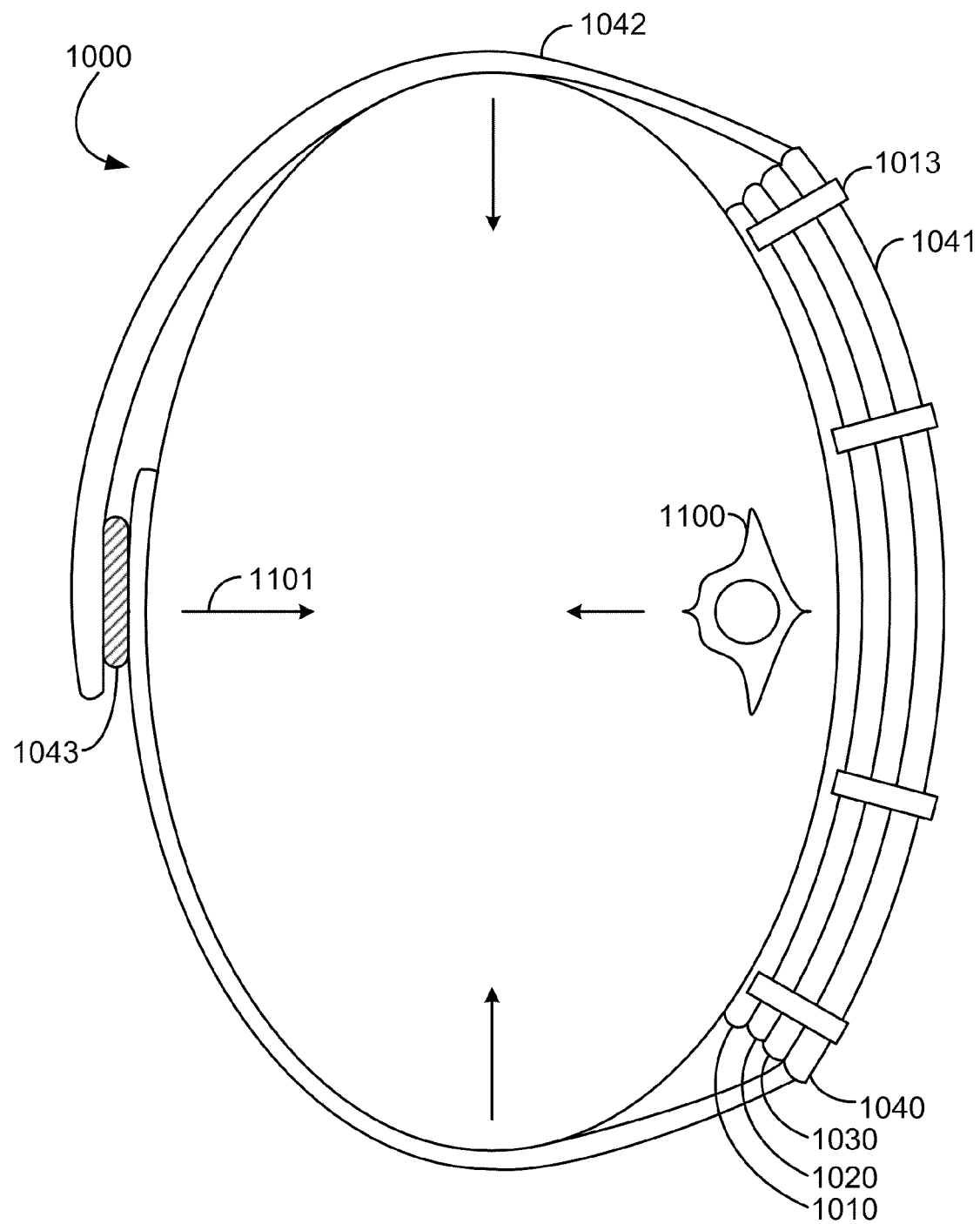
FIG. 11B shows a cross-section view of the therapeutic spinal column brace system secured to the therapy site of a therapy recipient in accordance with an embodiment of the present invention.

FIG. 11B shows a cross-section view of the Therapeutic Spinal Column Brace System 1000 secured to the therapy site of a therapy recipient in accordance with an embodiment of the present invention. The cross sectional view of FIG. 11B more clearly illustrates the Inward Compressive Force 1101 applied by the Therapeutic Spinal Column Brace System 1000. Additionally, the Rigid Spinal Column 1100 is illustrated to provide orientation of the Therapeutic Spinal Column Brace System 1000 in relation to the therapy recipient's body and clearly shows the various layers of the Therapeutic Spinal Column Brace System 1000. As seen, the Thermal Exchange Layer 1010 is situated in direct contact with the dorsal portion of the recipient's torso. The Compression Layer 1020 is next, followed by a Cushion Layer 1030 and finally the Outer layer 1040, including the Rigid Support Shell 1041, overlays all previous layers. Additionally, the Adjustable Elastic Straps 1013 are illustrated, showing how the Adjustable Elastic Straps 1013 aid in securing the components of the Therapeutic Spinal Column Brace System 1000 together.

Of course, these layers are not exhaustive, and additional layers may be included. Additionally, the layer sequence may be altered to elicit an appropriate therapeutic response. For instance, an additional Cushioning Layer 1030 may be incorporated between the Thermal Exchange Layer 1010 and the Compression Layer 1020 in order to increase therapy recipient's comfort. Alternatively, it may be possible to exclude the Compression Layer 1020, and instead include the compressive function of the Compression Layer 1020 into the Thermal Exchange Layer 1010. Alternatively, the Amalgamated Bladder 1700 may replace the Compression Layer 1020 and the Thermal Exchange Layer 1010.

The adjustable Straps 1042 circumvent the therapy recipient's trunk to meet on the recipient's abdomen. Straps 1042 may be made of an elastic material. In some embodiments, the Straps 1042 are designed to stretch to approximately 150%-200% of their unstretched length, however less elastic and more elastic Straps 1042 may be used. A surface of loops on the surface of Straps 1042 is adapted to detachably receive complementary Hooks 1043. The Hooks 1043 and loops are positioned so that the Hooks 1043 may engage the loops when the Outer Layer 1040 is wrapped around a therapy site. The Outer Layer 1040 may be adjusted to a desired tension and a corresponding level of compressive force that may be fixed by engaging the Hooks 1043 and the loops together. The Hooks 1043 and the loops may subsequently be disengaged, so that the tension may be adjusted, for instance, and reengaged at will. In some embodiments, a wrap lock, belt buckles, lacing or any other acceptable method may alternatively be used to secure the Outer Layer 1040 around the therapy recipient's torso.

Figure 11C:
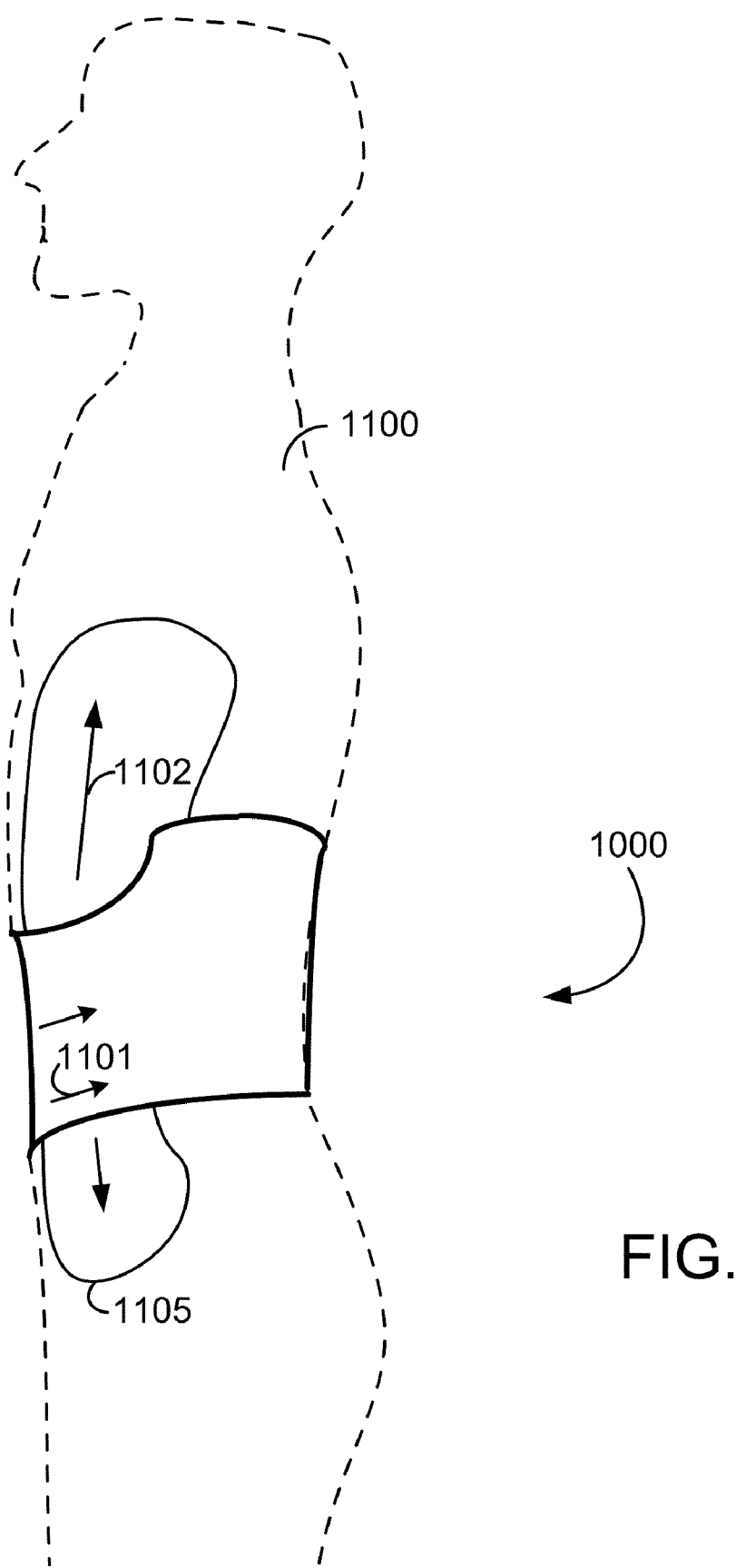
FIG. 11C shows a side cross-section view of the therapeutic spinal column brace system secured to the therapy site of a therapy recipient in accordance with an embodiment of the present invention.

FIG. 11C shows a side cross-section view of the Therapeutic Spinal Column Brace System 1000 including a Contrast Therapy System 10 secured to the therapy site of a therapy recipient in accordance with an embodiment of the present invention. The figure illustrates how the Inward Compressive Force 1101 generated by the Therapeutic Spinal Column Brace System 1000 forces the Internal Structures of the Abdomen 1105 to exert Vertical Pressure 1102, thereby providing internal support in addition to the external support provided by the Rigid Support Shell 1041 of the Outer Layer 1040.

FIG. 12 shows a view of the Thermal Exchange Bladder 1200 for use in the Therapeutic Spinal Column Brace System 1000 in accordance with an embodiment of the present invention. In FIG. 12 the Thermal Exchange Bladder 1200 is shown apart from the remainder of the Contrast Therapy System 10. As described above, the Thermal Exchange Bladder 1200 may be easily coupled and decoupled from the Reversible Tubing Assembly 58, which allows various different Therapy Pads to be used with the same Portable Control Unit 30. Each Thermal Exchange Bladder 1200 is designed to receive therapy fluid from the Mixing Valve 16, such as through the Fluidic Coupling Assembly 20, and return the therapy fluid to at least one of the Hot Reservoir 14 and the Cold Reservoir 12 (as shown schematically in FIG. 2). The Thermal Exchange Bladder 1200 returns fluid to the Portable Control Unit 30, and the returned fluid may be recirculated. Depending on the type of therapy being applied, returned fluid may be heated and/or cooled at the Portable Control Unit 30. The Therapeutic Spinal Column Brace System 1000 including the Contrast Therapy System 10 may include a return valve that selectively directs return fluid to the Hot Reservoir 14 and/or the Cold Reservoir 12, or the return fluid may be allowed to naturally flow to the lower pressure region.

The Thermal Exchange Bladder 1200 may include a flexible membrane of opposing faces that are welded together to define a channel system for directing the flow of therapy fluid along a desired Fluid Path 1205 within the Thermal Exchange Bladder 1200. For example, the faces are usually welded along a common Outer Perimeter 1201, sealing the faces together. A Division Weld 1203 may direct fluid through a substantial portion of the Thermal Exchange Bladder 1200 before returning to the Portable Control Unit 30. The Thermal Exchange Bladder 1200 may also include a plurality of Intermittent Welds 1202 that limit inflation of the bladder.

The Thermal Exchange Bladder 1200 facilitates thermal exchange between a therapy site and the therapy fluid. For example, when a cold therapy is administered, heat from a recipient's body may heat the therapy fluid, which in turn cools the therapy site of the recipient's body. Similarly, when a hot therapy is administered, the therapy fluid may transfer heat to the therapy site. The therapy may be enhanced by moistening the Thermal Exchange Bladder 1200 to provide a moist therapy. Furthermore, the fluid may also be pulsed through the Thermal Exchange Bladder 1200, adding a therapeutic massage aspect to the treatment.

In the illustrated embodiment, Thermal Exchange Bladder 1200 may be dimensioned to hold approximately 275 cubic centimeters of fluid within the bladder Volume 1204. However, the Volume 1204 of the Thermal Exchange Bladder 1200 may be controlled by changing the size of the Thermal Exchange Bladder 1200, and/or the amount of inflation the Intermittent Welds 1202 allow. Furthermore, the Thermal Exchange Bladder 1200 may be constructed from an at least partially elastic material, such as urethane, which may permit the Volume 1204 to change in response to the pressure of fluid within the Thermal Exchange Bladder 1200. In some embodiments, the Thermal Exchange Bladder 1200 may include a less elastic material that helps prevent stretching, such as a vinyl/urethane blend. In some embodiment the Thermal Exchange Bladder 1200 may be dimensioned to hold between 200 to 400 cubic centimeters of fluid within the bladder Volume 1204. This range of fluid volume provides the necessary balance between weight and thermal transfer.

As shown in FIG. 12, fluid may enter the Thermal Exchange Bladder 1200 at the Bladder Connector 1012, flow around the Division Weld 1203 and the Intermittent Welds 1202, and leave the Thermal Exchange Bladder 1200 at the Bladder Connector 1012. It is within the scope of the invention to reconfigure the Thermal Exchange Bladder 1200 to accommodate different Flow Paths 1205. For example, the Division Weld 1203, or Plural Division Welds 1203, may be used to direct the fluid through a series of switchbacks before returning to the output of the Bladder Connector 1012 as shown in FIG. 10. Small breaks may be included in the Division Weld 1203 to permit alternative Flow Paths 1205 if a primary Flow Path 1205 is blocked.

In some embodiment, the Thermal Exchange Bladder 1200 may be inflated as to press against the therapy recipient, thereby providing a compression therapy on the therapy site. The Pump 18 housed within the Portable Control Unit 30 may provide the fluid pressure required to inflate the Thermal Exchange Bladder 1200. By controlling the pressure within the Thermal Exchange Bladder 1200, the intensity of compression on the therapy site may be regulated. As such, the pressure within the Thermal Exchange Bladder 1200 may be held constant, thereby providing a steady compression on the therapy site. Alternatively, the pressure within the Thermal Exchange Bladder 1200 may be varied dynamically, thereby providing a therapeutic, massage-like pulsation on the therapy site. The Thermal Exchange Bladder 1200 may be inflated and subsequently depressurized in rapid succession to emulate a more rigorous vibrating therapy, or may be more slowly inflated and depressurized as is desirable. It may also be possible, in some embodiment, to provide very complicated compression cycles as is found to best suit the therapy recipients needs. Control over type and rate of compression therapy may be automated, or may be manually alterable.

FIG. 13A shows a top plan cutaway view of the Thermal Exchange Bladder 1200 within the Thermal Exchange Layer 1010 for use in the Therapeutic Spinal Column Brace System 1000 including the Contrast Therapy System 10 in accordance with an embodiment of the present invention. The Thermal Exchange Bladder 1200 is enclosed within an envelope; the face in contact with the therapy recipient comprises a Mesh 1011 material that facilitates thermal exchange with the therapy recipient. The Mesh 1011 may be permanently connected to the Thermal Exchange Bladder 1200 by stitching, an adhesive, and/or another suitable fastener. Alternatively, the Thermal Exchange Layer 1010 may incorporate an envelope that the Thermal Exchange Bladder 1200 may fit into non-permanently, enabling ease of cleaning The reverse face of the Thermal Exchange Layer 1010 includes a Solid Material 1300 as shown in FIG. 13B.

FIG. 13B shows a bottom plan view the Thermal Exchange Layer 1010 for use in the Therapeutic Spinal Column Brace System 1000 including a Contrast Therapy System 10 in accordance with an embodiment of the present invention. The Solid Material 1300 on the reverse face of the Thermal Exchange Layer 1010 usually includes a surface of loops that are adapted to detachably receive complementary hooks. The Solid Material 1300 may include neoprene or another insulating material thus limiting thermal exchange with the external environment that does not perform a therapeutic function, thereby increasing Thermal Exchange Layer 1010 efficiency. The Solid Material 1300 may be permanently connected to the Thermal Exchange Bladder 1200 by stitching, an adhesive, and/or another suitable fastener. Alternatively, the Thermal Exchange Layer 1010 may incorporate an envelope that the Thermal Exchange Bladder 1200 may fit into non-permanently, enabling ease of cleaning.

Additionally, regions of Hooks 1015 may exist to aid in securing the Thermal Exchange Layer 1010 to the Compression Layer 1020. The Hooks 1015 are positioned so that the Hooks 1015 may engage loops on the Compression Layer 1020 when the Thermal Exchange Layer 1010 is adjacent to it.

The Bladder Connecter 1012 protrudes from the bulk of the Thermal Exchange Layer 1010 thereby allowing for ready accessibility and easy coupling and decoupling to the Reversible Tubing Assembly 58.

Adjustable Straps 1013 may be permanently connected to the Mesh 1011 and Solid Material 1300 envelope by stitching, an adhesive, and/or another suitable fastener. As earlier stated, the Adjustable Straps 1013 may be made of elastic material. The amount of elasticity a particular Adjustable Strap 1013 has may be selected according to a desired application, or range of applications. In some embodiments, the Adjustable Straps 1013 are designed to stretch to approximately 150%-200% of their unstretched length, however less elastic and more elastic Adjustable Straps 1013 may be used. The Adjustable Straps 1013 may be variously sized, and are usually at least as long as required to wrap around the Compressive Layer 1020, the Cushion Layer 1030 and the Outer Layer 1040 in order to secure the various layers together firmly. Adjustable Straps 1013 usually include a surface of loops that are adapted to detachably receive complementary Hooks 1014. The Hooks 1014 and loops are positioned so that the Hooks 1014 may engage the loops when the Adjustable Straps 1013 are wrapped around the various layers. The Adjustable Straps 1013 may be adjusted to desired tensions and may be fixed by engaging the Hooks 1014 and the loops together. The Hooks 1014 and loops may subsequently be disengaged, so that the tension may be adjusted, for instance, and reengaged at will. In some embodiments, a wrap lock, or other appropriate system, may alternatively be used to secure the Thermal Exchange Layer 1010, Compressive Layer 1020, the Cushion Layer 1030 and the Outer Layer 1040 together.

In some embodiments, the Thermal Exchange Layer 1010 may be constructed with disposable materials. For example, Thermal Exchange Layer 1010 configured for a single use may be constructed from disposable materials, which are usually less expensive than reusable materials. Disposable Thermal Exchange Layer 1010 may be particularly useful in emergency, trauma, or post surgery situations, in which a therapy recipient may bleed onto the Thermal Exchange Layer 1010. The ability to control the temperature of the Thermal Exchange Layer 1010, either reusable or disposable, may increase the Thermal Exchange Layer 1010 effectiveness as a wound dressing. Disposable materials may include less resilient versions of reusable materials and/or completely different materials. In some embodiments, disposable materials may include apertured, breathable, elastomeric and/or embossed films, as well as nonwoven laminates. Thermal Exchange Layer 1010 may alternatively be configured to be washable, such as by a laundry machine, and therefore may be sanitarily reused.

Additionally, the Thermal Exchange Bladder 1200 and corresponding Thermal Exchange Layer 1010 may vary in shape and size in order to accommodate particular therapeutic desires or Therapeutic Spinal Column Brace System 1000 configurations.

FIG. 13C shows a cross-sectional view of the Thermal Exchange Layer 1010 in accordance with an embodiment of the present invention. The FIG. 13C more clearly illustrates the Thermal Exchange Bladder 1200 geometry include within the Thermal Exchange Layer 1010. The Intermittent Welds 1202 provide strength to the Thermal Exchange Bladder 1200 as well as restrict the expansion of the Thermal Exchange Bladder's Volume 1204. The top face is covered by Mesh 1011 that promotes thermal transfer to the therapy site. The bottom face of the bladder envelope includes Solid Material 1300 for enclosing the Thermal Exchange Bladder 1200, providing thermal insulation, and as additional structural support for the Thermal Exchange Layer 1010.

Figure 14:
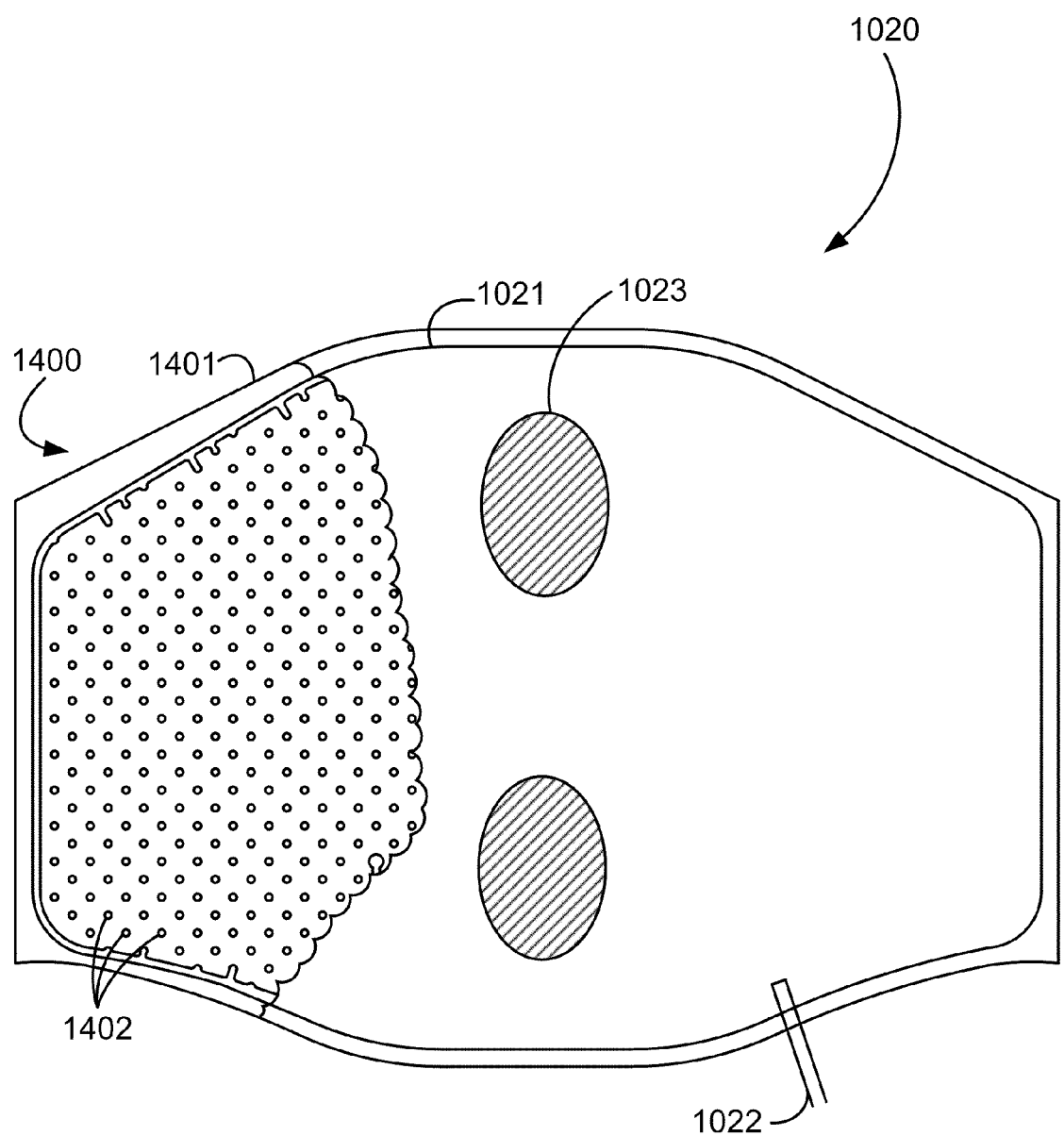
FIG. 14 shows a top plan cutaway view of a compression layer for use in a therapeutic spinal column brace system in accordance with an embodiment of the present invention.

FIG. 14 shows a top plan cutaway view of the Compression Layer 1020 for use in the Therapeutic Spinal Column Brace System 1000 in accordance with an embodiment of the present invention. The Compression Layer 1020 includes a Compression Bladder 1400 and a Compression Bladder Envelope 1021. The Surface of the Compression Bladder Envelope 1021 may be covered in loops adapted to releasably receive complementary hooks to secure the Compression Layer 1020 to the Thermal Exchange Layer 1010. Additionally, there may be a region of Hooks 1023, adapted to releasably receive complementary loops on the Cushion Layer 1030 Surface 1033. A Compression Bladder Connector 1022 allows for inflation of the Compression Bladder 1400 with air or other fluid.

The Compression Bladder 1400 may include a flexible membrane of opposing faces that are welded together to define a volume for pressurized expansion. For example, the faces are usually welded along a common Outer Perimeter 1401, sealing the faces together. The Compression Bladder 1400 may also include a plurality of Intermittent Welds 1402 that limit inflation of the bladder.

In the illustrated embodiment, Compression Bladder 1400 may be dimensioned to hold approximately 275 cubic centimeters of fluid within the bladder volume. However, the Volume 1404 of the Compression Bladder 1400 may be controlled by changing the size of the Compression Bladder 1400, and/or the amount of inflation the Intermittent Welds 1402 allow. Furthermore, the Compression Bladder 1400 may be constructed from an at least partially elastic material, such as urethane, which may permit the volume to change in response to the pressure of fluid within the Compression Bladder 1400. In some embodiments, the Compression Bladder 1400 may include a less elastic material that helps prevent stretching, such as a vinyl/urethane blend.

A pressurizing pump (not shown) supplies the pressurizing fluid through the Compression Bladder Connector 1022, and regulates the pressure within the Compression Bladder 1400. The pressurizing fluid may include air, water or any other suitable fluid. The Compression Bladder 1400 may be inflated as to press against the therapy recipient, thereby providing a compression therapy on the therapy site. By controlling the pressure within the Compression Bladder 1400, the intensity of compression on the therapy site may be regulated. As such, the pressure within the Compression Bladder 1400 may be held constant, thereby providing a steady compression on the therapy site. Alternatively, the pressure within the Compression Bladder 1400 may be varied dynamically, thereby providing a therapeutic, massage-like pulsation on the therapy site. The Compression Bladder 1400 may be inflated and subsequently depressurized in rapid succession to emulate a more rigorous vibrating therapy, or may be more slowly inflated and depressurized as is desirable. It may also be possible, in some embodiment, to provide very complicated compression cycles as is found to best suit the therapy recipients needs. Control over type, and rate, of compression therapy may be automated, or may be manually alterable.

FIG. 15 shows an isometric view of the Cushion Layer 1030 for use in the Therapeutic Spinal Column Brace System 1000 in accordance with an embodiment of the present invention. The Cushion Layer 1030 may utilize a variety of materials that provide dissipation of any pressure points that may exist, thereby increasing comfort for the therapy recipient. Comfort to the recipient is of extreme importance because any wearable therapy system is dependent upon prolonged and consistent use by the therapy recipient. By adding to the comfort of the system the chances of continued use of the Therapeutic spinal column brace system Assembly 1000 is increased.

Additionally, the action of equalizing the force across the entire therapy site ensures that there is never any disruption, or asymmetry, of the Fluid Path 1205. This enables complete and continuous thermal therapy over the entire therapy site and an associated increase in therapy effectiveness.

Furthermore, by distributing the force between the therapy recipient and the Therapeutic spinal column brace system Assembly 1000, the Cushion Layer 1030 ensures an intimate fit between the Therapy Exchange Layer 1010 and the therapy site. This intimate fit guarantees that there are no voids between the Mesh 1011 face of the Therapy Exchange Layer 1010 and the therapy site, thereby maximizing thermal exchange. Optimal thermal exchange is also required for effective contrast therapy. Additionally, the intimate fit ensures that the Therapeutic spinal column brace system Assembly 1000 is held securely against the therapy site. Proper fit is also a requisite for recipient comfort and effectiveness of therapy, since the therapy system remains in constant contact with the therapy site.

Cushion Layer 1030 may have a Surface 1033 covered in loops adapted to releasably receive complementary Hooks 1023 from the Compression Layer 1020. Additionally, a region of Hooks 1032 may exist to releasably receive complementary Loops 1044 on the Rigid Support Shell 1041.

Cushion Layer 1030 may include Voids 1031 to increase ventilation, reduce pressure in certain locations, increase flexibility or for any other purpose.

FIG. 16 shows an isometric view of the Outer Layer 1040 for use in a Therapeutic Spinal Column Brace System 1000 in accordance with an embodiment of the present invention. The Outer Layer 1040 includes Adjustable Straps 1042 for securing the Therapeutic Spinal Column Brace System 1000 to the therapy recipient, and a Rigid Support Shell 1041 for providing Spinal Column 1100 support.

The Rigid Support Shell 1041 may be metal, plastic, ceramic, leather or any other material, or combination of materials, that may provide some degree of inflexibility. The Rigid Support Shell 1041 may provide uniform rigidity or one or more gradients of stiffness to allow for limited movement in some planes or torsions, but more extensive movement along other planes and rotations. Additionally, the Rigid Support Shell 1041 may be adapted to provide dynamic support of the therapy site. An example of this would be increasing rigidity of the Rigid Support Shell 1041 as the Rigid Support Shell 1041 is deformed, thus requiring ever increasing force to continue the deformation.

Additionally, the Rigid Support Shell 1041 may utilize one or more Support Braces 1045. Support Braces 1045 may be metal, plastic, ceramic, leather or any other material, or combination of materials, that may provide some degree of inflexibility. Some Support Braces 1045 may support along the axis of the spinal column and may provide unilateral vertical support. Alternatively, Support Braces 1045 may be of more elaborate in design to provide additional horizontal and/or torsion rigidity, and/or dynamic support. An example of such a Support Brace 1045 may include a honeycomb structure with composite materials, such as a metal core within plastic casing.

Moreover, removable Struts 1600 may be incorporated into the Support Braces 1045. Removable Struts 1600 provide the advantage of allowing the therapy recipient, health care provider, or the retailer to alter the magnitude and character of the support as is required to optimize therapy. For instance, a post operational therapy recipient may require a large amount of support immediately after surgery; however it may be desirable to gradually reduce support as healing progresses to endure mobility and retention of muscle at the therapy site. In such a circumstance, Struts 1600 may be systematically removed over time from the Support Braces 1045 to allow for gradual reduction of support.

The Rigid Support Shell 1041 may be custom fitted to the therapy recipient, or may be adapted to fit a variety of body types. Likewise, there may be specific designs of the Rigid Support Shell 1041 adapted to fit specific genders. Alternatively, the Rigid Support Shell 1041 may be designed to fit any gender. In some embodiment, the Rigid Support Shell 1041 may include segments of flexible material to ensure a secure fit on a greater variety of body types.

The Rigid Support Shell 1041 may include multiple designs to extend as high up the length of the Spinal Column 1100 as is required to provide sufficient support and thus superior therapy. In some embodiment, the Rigid Support Shell 1041 encircles only the dorsal side of the therapy recipient. The width of the Rigid Support Shell 1041 may be increased or decreased as is necessary to provide sufficient support for effective therapy.

As stated earlier, the adjustable Straps 1042 circumvent the therapy recipient's trunk to meet on the recipient's abdomen. Straps 1042 may be permanently connected to the Rigid Support Shell 1041 by stitching, an adhesive, and/or another suitable fastener. Straps 1042 may be made of an elastic material. In some embodiments, the Straps 1042 are designed to stretch to approximately 150%-200% of their unstretched length, however less elastic and more elastic Straps 1042 may be used. A surface of loops on the surface of Straps 1042 is adapted to detachably receive complementary Hooks 1043. The Hooks 1043 and loops are positioned so that the Hooks 1043 may engage the loops when the Outer Layer 1040 is wrapped around a therapy site. The Outer Layer 1040 may be adjusted to a desired tension and a corresponding level of compressive force that may be fixed by engaging the Hooks 1043 and the loops together. The Hooks 1043 and the loops may subsequently be disengaged, so that the tension may be adjusted, for instance, and reengaged at will. In some embodiment, Finger Pockets 1601 may be included at the extremity of the Straps 1042 in order to aid in the donning of the Therapeutic Spinal Column Brace 1000. The Finger Pockets 1601 allow for greater leverage by the therapy recipient, thus enabling ease of engaging and disengaging Hooks 1043 and the loops for tensional adjustment. In some embodiments, a wrap lock, belt buckles, lacing or any other acceptable method may alternatively be used to secure the Outer Layer 1040 around the therapy recipient's torso.

Additional adjustable Straps 1042 may be included into the Outer Layer 1040 as is necessary. For instance, chest straps may be required for elongated Therapeutic Spinal Column Braces 1000 that extend the length of the Spinal Column 1100. Such chest straps in conjunction with an elongated Rigid Support Shell 1041 can supply a greater range of Spinal Column 1100, and associated musculoskeletal tissue, support.

A region of Loops 1044 on the Rigid Support Shell 1041 may releasably receive the Hooks 1032 from the Cushion Layer 1030 thereby aiding in securing the layers of the Therapeutic Spinal Column Brace 1000 together.

FIG. 17A shows a cutaway view of an Amalgamated Bladder 1700 for use in the Therapeutic Spinal Column Brace System 1000 in accordance with an embodiment of the present invention. In some embodiment, the Amalgamated Bladder 1700 combines both a Fluid Layer 1710 and a Pneumatic Layer 1720. The Fluid Layer 1710 functions similarly equivalent to the Thermal Exchange Bladder 1200 and may provide thermal therapy to the therapy site. The Pneumatic Layer 1720 likewise functions similarly equivalent to the Compression Bladder 1400 and may provide compression to the therapy site. Thus, the Amalgamated Bladder 1700 may replace both the Thermal Exchange Layer 1010 and the Compression Layer 1020 in some embodiment. The Amalgamated Bladder 1700 may be placed in an envelope of mesh or other suitable material. The Fluid Layer 1710 surface of the Amalgamated Bladder 1700 may be placed against the therapy site to promote efficient thermal transfer. The Pneumatic Layer 1720 thus presses the Fluid Layer 1710 against the therapy site and provides thermal insulation for the Fluid Layer 1710, limiting thermal exchange with the external environment that does not perform a therapeutic function, and thereby increasing Fluid Layer 1710 efficiency.

Figure 17B:
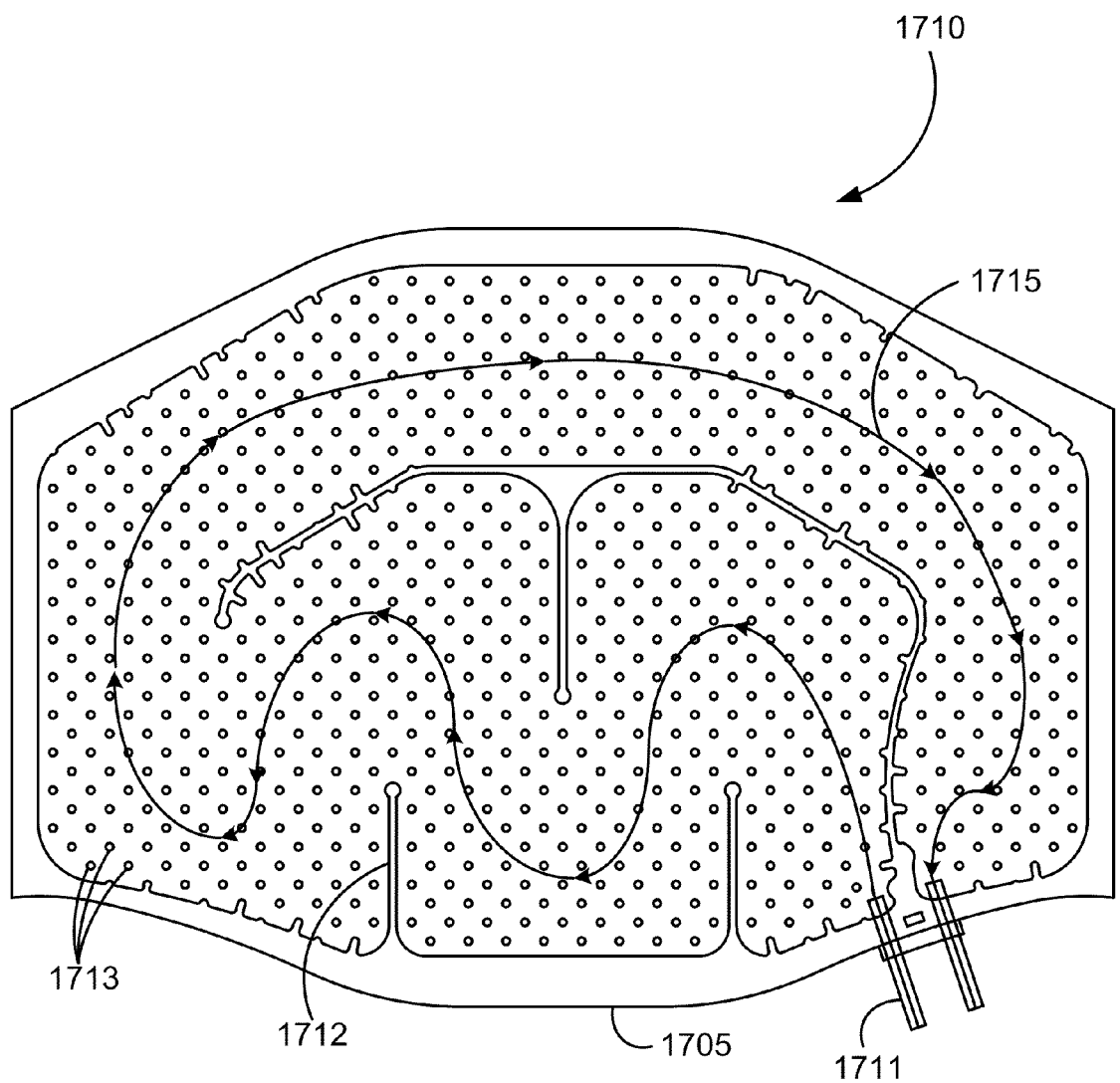
FIG. 17B shows a bottom plan view of an amalgamated bladder for use in a therapeutic spinal column brace system in accordance with an embodiment of the present invention.

FIG. 17B shows the Fluid Layer 1710 of the Amalgamated Bladder 1700 for use in the Therapeutic Spinal Column Brace System 1000 in accordance with an embodiment of the present invention. In some embodiment, the Amalgamated Bladder 1700 may include structures substantially similar to the Thermal Exchange Bladder 1200, and may include flexible membranes of opposing faces that are welded together to define a channel system for directing the flow of therapy fluid along a desired Fluid Path 1715. For example, the faces are usually welded along a common Outer Perimeter 1705, sealing the faces together. A Division Weld 1712 may direct fluid through a substantial portion of the Fluid Layer 1710 before returning to the Portable Control Unit 30. The Amalgamated Bladder 1700 may also include a plurality of Intermittent Welds 1704 that limit inflation of the Amalgamated Bladder 1700.

In FIG. 17B the Fluid Layer 1710 is shown apart from the remainder of the Contrast Therapy System 10. The Fluid Layer 1710 may be easily coupled and decoupled from the Reversible Tubing Assembly 58, which allows various different Therapy Pads to be used with the same Portable Control Unit 30. Each Fluid Layer 1710 is designed to receive therapy fluid from the Mixing Valve 16, such as through the Fluidic Coupling Assembly 20, and return the therapy fluid to at least one of the Hot Reservoir 14 and the Cold Reservoir 12 (as shown schematically in FIG. 2). The Fluid Layer 1710 returns fluid to the Portable Control Unit 30, and the returned fluid may be recirculated. Depending on the type of therapy being applied, returned fluid may be heated and/or cooled at the Portable Control Unit 30. The Therapeutic Spinal Column Brace System 1000 including the Contrast Therapy System 10 may include a return valve that selectively directs return fluid to the Hot Reservoir 14 and/or the Cold Reservoir 12, or the return fluid may be allowed to naturally flow to the lower pressure region.

The Fluid Layer 1710 facilitates thermal exchange between a therapy site and the therapy fluid. For example, when a cold therapy is administered, heat from a recipient's body may heat the therapy fluid, which in turn cools the therapy site of the recipient's body. Similarly, when a hot therapy is administered, the therapy fluid may transfer heat to the therapy site. The therapy may be enhanced by moistening the Amalgamated Bladder 1700 to provide a moist therapy. Furthermore, the fluid may also be pulsed through the Fluid Layer 1710, adding a therapeutic massage aspect to the treatment.

In the illustrated embodiment, Fluid Layer 1710 may be dimensioned to hold approximately 275 cubic centimeters of fluid within the bladder volume. However, the volume of the Fluid Layer 1710 may be controlled by changing the size of the Fluid Layer 1710, and/or the amount of inflation the Intermittent Welds 1704 allow. Furthermore, the Amalgamated Bladder 1700 may be constructed from an at least partially elastic material, such as urethane, which may permit the volume of the Fluid Layer 1710 to change in response to the pressure of fluid within the Fluid Layer 1710. In some embodiments, the Amalgamated Bladder 1700 may include a less elastic material that helps prevent stretching, such as a vinyl/urethane blend. In some embodiment, the Fluid Layer 1710 may be dimensioned to hold between 200 to 400 cubic centimeters of fluid within the Fluid Layer 1710 volume. This range of fluid volume provides the necessary balance between weight and thermal transfer.

As shown in FIG. 17B, fluid may enter the Fluid Layer 1710 at the Fluid Layer Connector 1711, flow around the Division Weld 1712 and the Intermittent Welds 1705, and leave the Fluid Layer 1710 at the Fluid Layer Connector 1711. It is within the scope of the invention to reconfigure the Fluid Layer 1710 to accommodate different Flow Paths 1715. For example, the Division Weld 1712, or Plural Division Welds 1712, may be used to direct the fluid through a series of switchbacks before returning to the output of the Fluid Layer Connector 1711. Small breaks may be included in the Division Weld 1712 to permit alternative flow paths if a primary Flow Path 1715 is blocked.

Figure 17C:
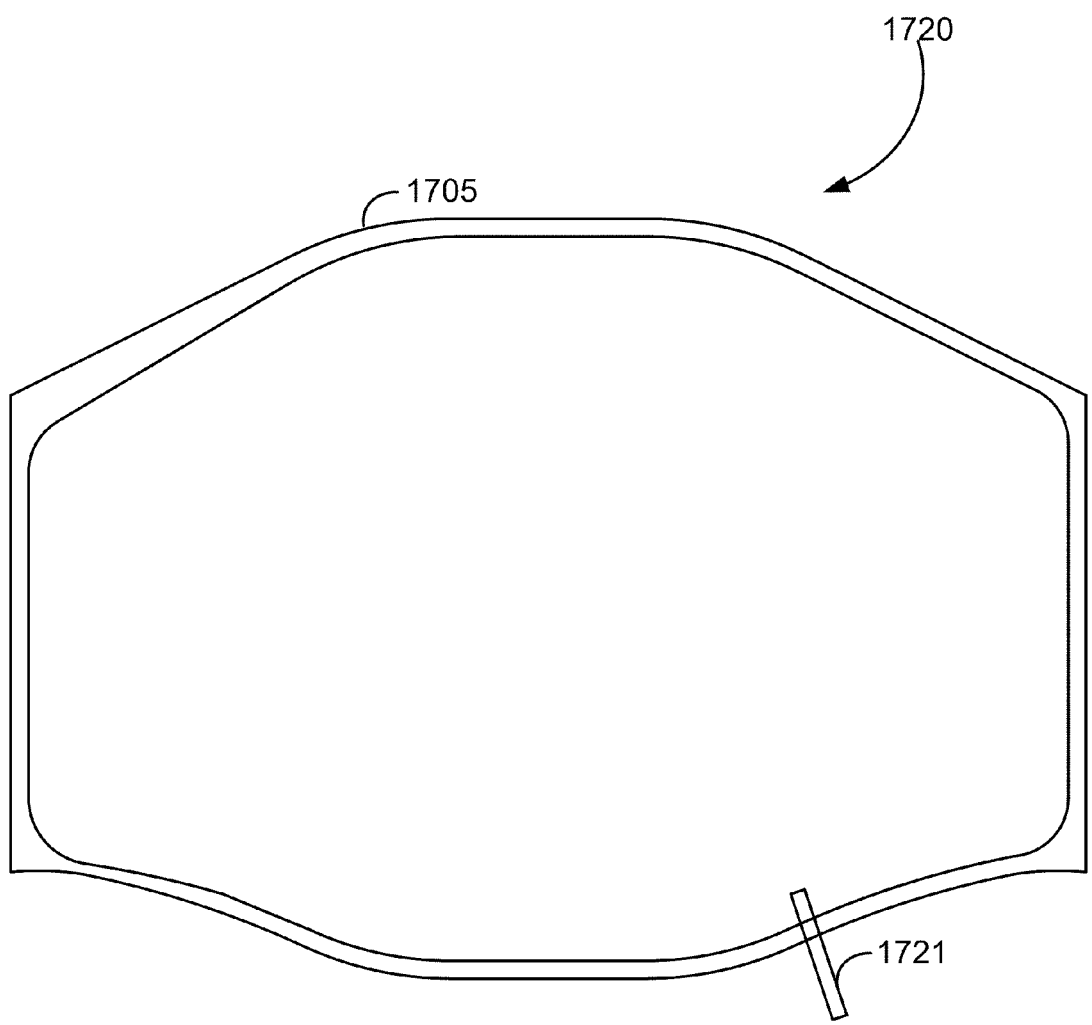
FIG. 17C shows an isometric view of a fluid layer of an amalgamated bladder for use in a therapeutic spinal column brace system in accordance with an embodiment of the present invention.

FIG. 17C shows the Pneumatic Layer 1720 of the Amalgamated Bladder 1700 for use in the Therapeutic Spinal Column Brace System 1000 in accordance with an embodiment of the present invention. The Pneumatic Layer 1720 may be pressurized with a fluid through the Pneumatic Connecter 1721, inflating the Pneumatic Layer 1720 and thus providing compression upon the therapy site. By controlling the pressure within the Pneumatic Layer 1720, the intensity of compression on the therapy site may be regulated. As such, the pressure within the Pneumatic Layer 1720 may be held constant, thereby providing a steady compression on the therapy site. Alternatively, the pressure within the Pneumatic Layer 1720 may be varied dynamically, thereby providing a therapeutic, massage-like pulsation on the therapy site. The Pneumatic Layer 1720 may be inflated and subsequently depressurized in rapid succession to emulate a more rigorous vibrating therapy, or may be more slowly inflated and depressurized as is desirable. It may also be possible, in some embodiment, to provide very complicated compression cycles as is found to best suit the therapy recipients needs. Control over type and rate of compression therapy may be automated, or may be manually alterable.

Figure 17D:
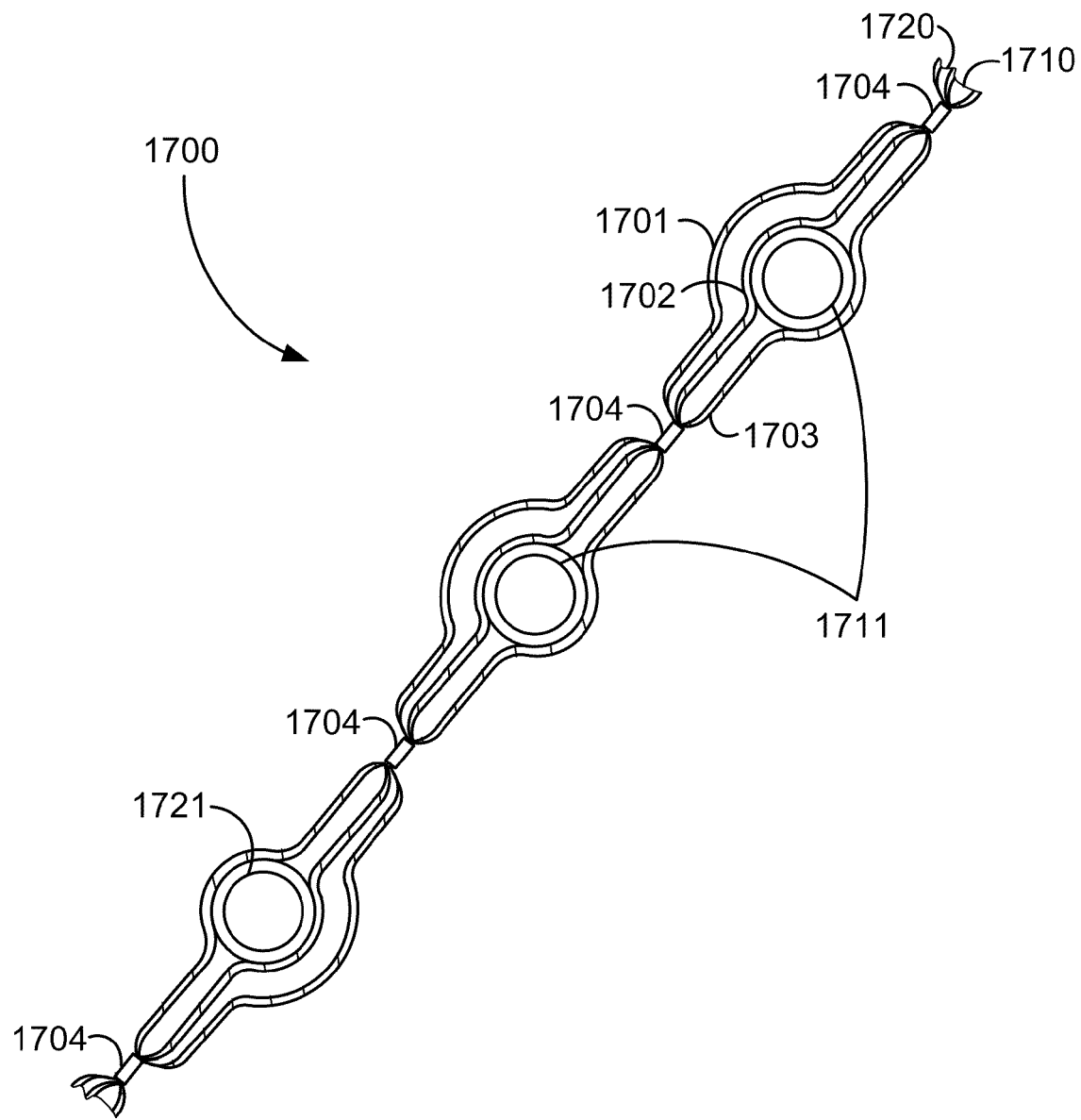
FIG. 17D shows a cross sectional view of an amalgamated bladder for use in a therapeutic spinal column brace system in accordance with an embodiment of the present invention.

FIG. 17D shows a cross sectional view of the Amalgamated Bladder 1700 for use in the Therapeutic Spinal Column Brace System 1000 in accordance with an embodiment of the present invention. In some embodiment, the Amalgamated Bladder 1700 may include a First Membrane 1701, a Second Membrane 1702 and a Third Membrane 1703 sealed around the Outer Perimeter 1705. The First Membrane 1701 and Second Membrane 1702 may define the Pneumatic Layer 1720 volume for pressurized expansion. The Second Membrane 1702 and Third Membrane 1703 may define the Fluid Layer 1710 volume for therapeutic fluid flow. The First Membrane 1701, Second Membrane 1702 and Third Membrane 1703 may additionally be welded together at the Intermittent Welds 1704 to provide durability to the Amalgamated Bladder 1700 and prevent over inflation of the Fluid Layer 1710 or the Pneumatic Layer 1720. The First Membrane 1701, Second Membrane 1702 and Third Membrane 1703 may be made of the same material, or may include different materials depending upon the characteristics desired. For instance, it may be desired that the First Membrane 1701 be more elastic than the Second Membrane 1702 or Third Membrane 1703, thereby allowing for greater expansion of the Pneumatic Layer 1720.

The Fluid Layer Connecter Tubes 1711 may be seen inserting the Amalgamated Bladder 1700 between the Second Membrane 1702 and Third Membrane 1703, thereby providing therapy fluid to the Fluid Layer 1710. Likewise, the Pneumatic Connector 1721 may insert between the Second Membrane 1702 and First Membrane 1701, thereby providing pressure control to the Pneumatic Layer 1720.

Additionally, the Amalgamated Bladder 1700 may vary in shape and size in order to accommodate particular therapeutic desires or Therapeutic Spinal Column Brace System 1000 configurations.

In some embodiments, the Amalgamated Bladder 1700 may be constructed with disposable materials. For example, Amalgamated Bladder 1700 configured for a single use may be constructed from disposable materials, which are usually less expensive than reusable materials. The disposable Amalgamated Bladder 1700 may be particularly useful in emergency, trauma, or post surgery situations, in which a therapy recipient may bleed onto the Amalgamated Bladder 1700. The ability to control the temperature of the Fluid Layer 1710, either reusable or disposable, may increase the Amalgamated Bladder's 1700 effectiveness as a wound dressing. Disposable materials may include less resilient versions of reusable materials and/or completely different materials. In some embodiments, disposable materials may include apertured, breathable, elastomeric and/or embossed films, as well as nonwoven laminates. Amalgamated Bladder 1700 may alternatively be configured to be washable, such as by a laundry machine, and therefore may be sanitarily reused.

II. Second Embodiment

FIGS. 18A to 22 illustrate a second embodiment for a Spinal Column Brace which includes an Interchangeable Lumbar Contrast Therapy Pad 1900 for increased utility, mobility and comfort. This system may enable contrast therapy and support to be applied to the lower back. A streamlined profile and short umbilical enables the Interchangeable Lumbar Contrast Therapy Pad 1900 to be detached from the Contrast Therapy System 10 when therapy is not needed, and yet enables the wearer to continue wearing the brace for support purposes. In fact, the design of this embodiment of the spinal column brace is versatile enough to be worn under clothing without being noticeable in many cases. Thus, this brace design promotes long durational usage of the brace in a wide range of circumstances, both clinical and during everyday activities.

Figure 18A:
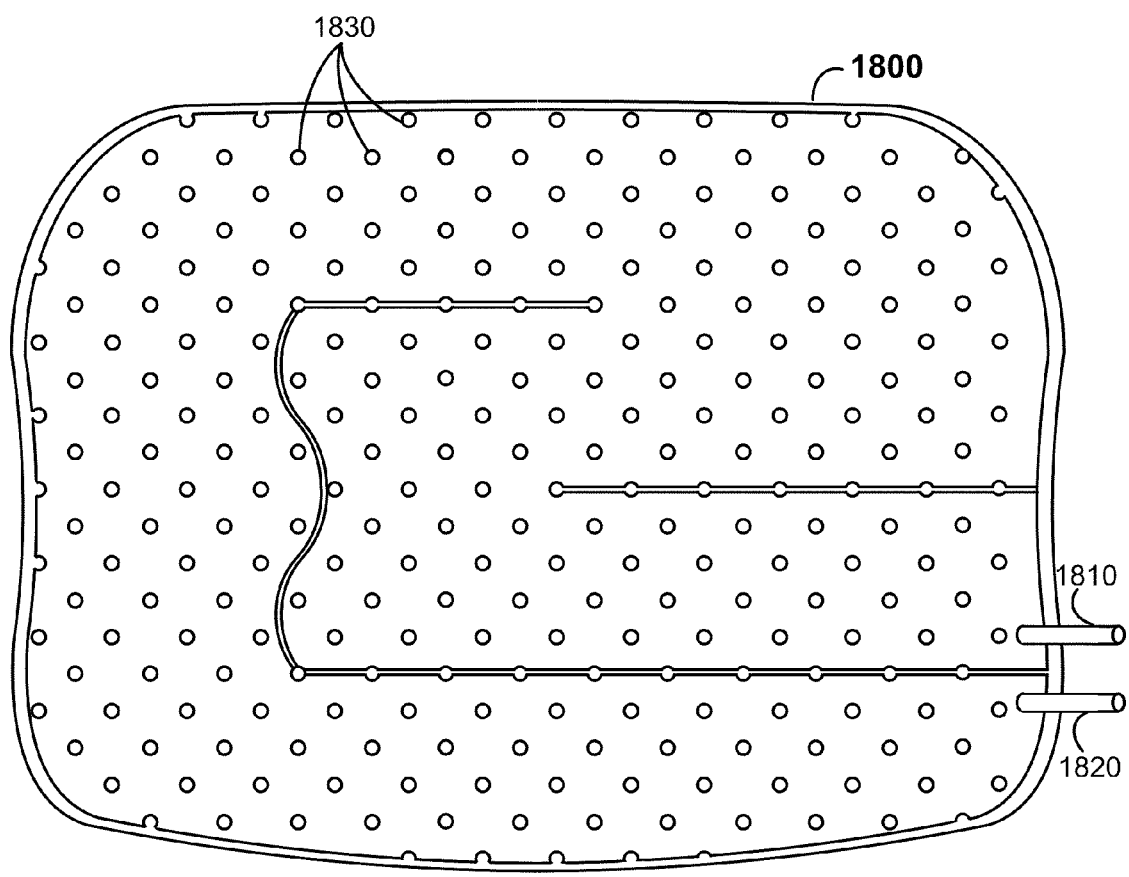
FIG. 18A illustrates another fluid bladder design for use in an interchangeable lumbar contrast therapy pad in accordance with an embodiment of the present invention.

FIG. 18A illustrates the Therapy Bladder 1800 design for use in the Interchangeable Lumbar Contrast Therapy Pad 1900 in accordance with an embodiment of the present invention. This Therapy Bladder 1800 includes a different fluid path than the previous pad designs. The purpose of this modified pad layout is to enable a smaller pad capable of fitting the Rigid Back Support System 2000 yet achieving near uniform heating and cooling of the therapy site.

As with other thermal exchange bladders, the Therapy Bladder 1800 is designed to receive therapy fluid from the Mixing Valve 16, such as through the Fluidic Coupling Assembly 20, and return the therapy fluid to at least one of the Hot Reservoir 14 and the Cold Reservoir 12 (as shown schematically in FIG. 2). The Therapy Bladder 1800 returns fluid to the Portable Control Unit 30, and the returned fluid may be recirculated. Depending on the type of therapy being applied, returned fluid may be heated and/or cooled at the Portable Control Unit 30. The Brace System including the Contrast Therapy System 10 may include a return valve that selectively directs return fluid to the Hot Reservoir 14 and/or the Cold Reservoir 12, or the return fluid may be allowed to naturally flow to the lower pressure region.

The Therapy Bladder 1800 may include a flexible membrane of opposing faces that are welded together to define a channel system for directing the flow of therapy fluid along a desired Fluid Path 1840 within the Therapy Bladder 1800. For example, as with previous bladder designs, the faces are usually welded along a common outer perimeter, sealing the faces together. A division weld may direct fluid through a substantial portion of the Therapy Bladder 1800 before returning to the Portable Control Unit 30. The Therapy Bladder 1800 may also include a plurality of Intermittent Welds 1830 that limit inflation of the bladder.

The Therapy Bladder 1800 facilitates thermal exchange between a therapy site and the therapy fluid. For example, when a cold therapy is administered, heat from a recipient's body may heat the therapy fluid, which in turn cools the therapy site of the recipient's body. Similarly, when a hot therapy is administered, the therapy fluid may transfer heat to the therapy site. The therapy may be enhanced by moistening the Therapy Bladder 1800 to provide a moist therapy. Furthermore, the fluid may also be pulsed through the Therapy Bladder 1800, adding a therapeutic massage aspect to the treatment.

The volume of fluid designed to circulate through the Therapy Bladder 1800 is dependent upon sizing. Differently sized Interchangeable Lumbar Contrast Therapy Pad 1900 may be offered to fit a particularly dimensioned wearer. The size of the Therapy Bladder 1800 may likewise be varied to fit the respective sized Interchangeable Lumbar Contrast Therapy Pad 1900. The fluid volume may further be controlled by changing the amount of inflation the Intermittent Welds 1830 allow. Furthermore, the Therapy Bladder 1800 may be constructed from an at least partially elastic material, such as urethane, which may permit the volume to change in response to the pressure of fluid within the Therapy Bladder 1800. In some embodiments, the Therapy Bladder 1800 may include a less elastic material that helps prevent stretching, such as a vinyl/urethane blend. In some embodiment, the Therapy Bladder 1800 may be dimensioned to hold between 200 to 400 cubic centimeters of fluid within the bladder volume. This range of fluid volume provides the necessary balance between weight and thermal transfer.

Figure 18B:
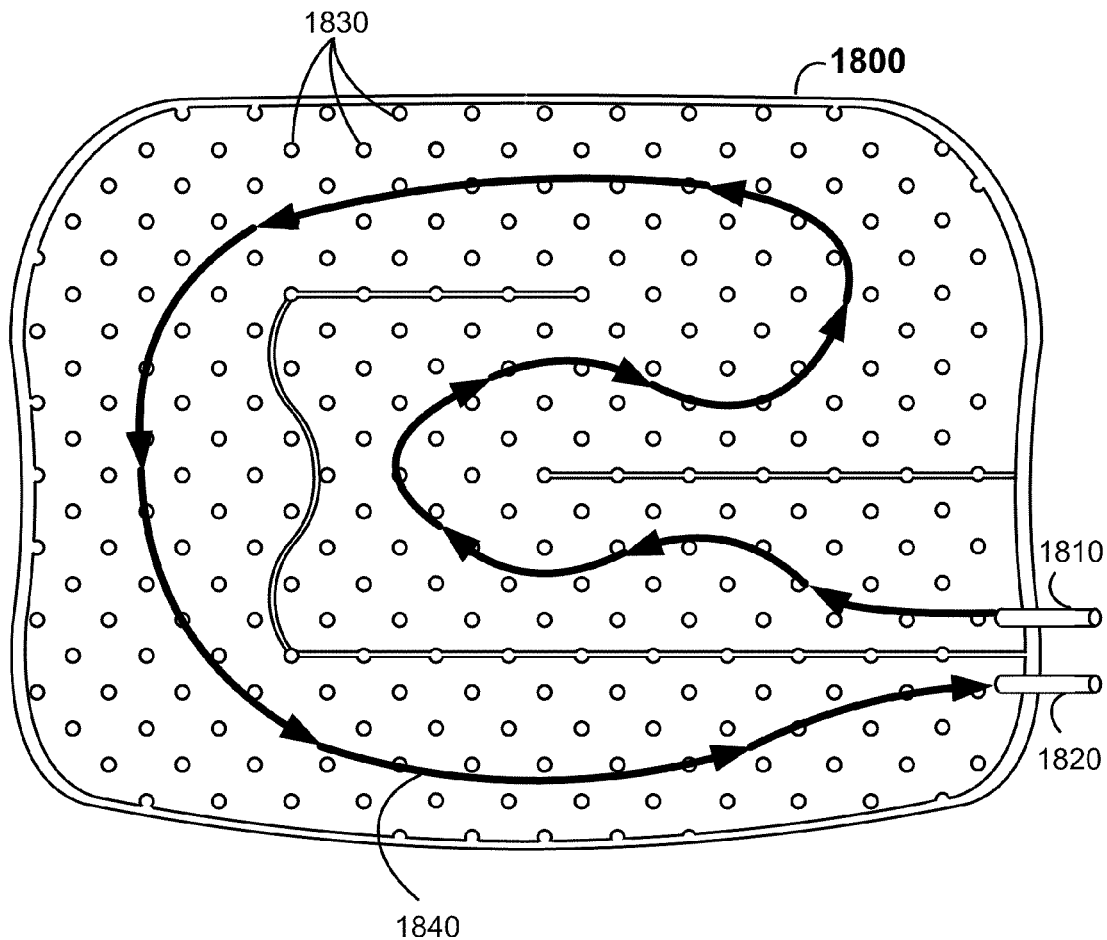
FIG. 18B illustrates the fluid bladder design of FIG. 18A including an illustration of a functional fluid pathway for use in the interchangeable lumbar contrast therapy pad in accordance with an embodiment of the present invention.

At FIG. 18B, the divisional weld is seen defining the Fluid Pathway 1840. This fluid pathway may begin at the Inlet Tube 1810 and travel throughout the Therapy Bladder 1800, eventually exiting the Therapy Bladder 1800 via the Outlet Tube 1820. This tortuous pathway enables near uniformity of fluid flow throughout the volume of the Therapy Bladder 1800. Fluid flow uniformity is necessary to prevent pad kinks and ensure temperature consistency. It is within the scope of the invention to reconfigure the Therapy Bladder 1800 to accommodate a different Flow Pathway 1840. For example, the division weld, or plural division welds, may be used to direct the fluid through a series of switchbacks before returning to the output of the bladder connector. Also, Small breaks may be included in the division weld to permit alternative flow paths if a primary Flow Pathway 1840 is blocked.

As with other bladder designs, in some embodiment, the Therapy Bladder 1800 may be inflated as to press against the therapy recipient, thereby providing a compression therapy on the therapy site. The Pump 18 housed within the Portable Control Unit 30 may provide the fluid pressure required to inflate the Therapy Bladder 1800. By controlling the pressure within the Therapy Bladder 1800, the intensity of compression on the therapy site may be regulated. As such, the pressure within the Therapy Bladder 1800 may be held constant, thereby providing a steady compression on the therapy site. Alternatively, the pressure within the Therapy Bladder 1800 may be varied dynamically, thereby providing a therapeutic, massage-like pulsation on the therapy site. The Therapy Bladder 1800 may be inflated and subsequently depressurized in rapid succession to emulate a more rigorous vibrating therapy, or may be more slowly inflated and depressurized as is desirable. It may also be possible, in some embodiment, to provide very complicated compression cycles as is found to best suit the therapy recipients needs. Control over type and rate of compression therapy may be automated, or may be manually alterable.

Figure 19A:
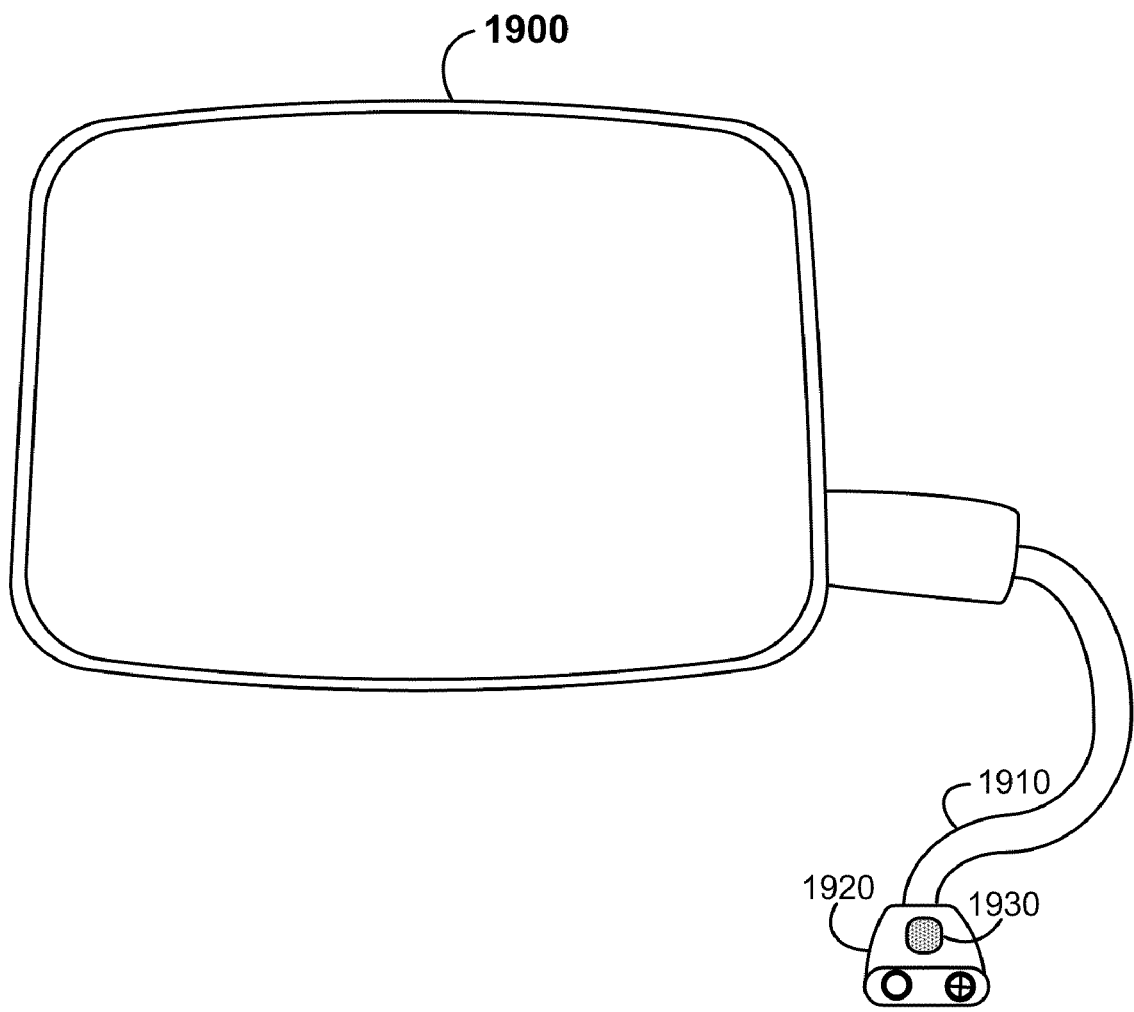
FIG. 19A illustrates the interchangeable lumbar contrast therapy pad in accordance with an embodiment of the present invention.

FIG. 19A illustrates the Interchangeable Lumbar Contrast Therapy Pad 1900 in accordance with an embodiment of the present invention. The Interchangeable Lumbar Contrast Therapy Pad 1900 includes the main pad, an Umbilical 1910 and a Fluid Coupler 1920. The Fluid Coupler 1920 may include Hook Material 1930 thereby enabling reversible coupling of the Fluid Coupler 1920 to any suitable loop materials. In some embodiments, the length of the Umbilical 1910 may be relatively short (roughly 18 inches) thereby ensuring the Fluid Coupler 1920 is easily within reach of the user at all times. Additionally, when the Interchangeable Lumbar Contrast Therapy Pad 1900 is decoupled from the Contrast Therapy System 10, the short Umbilical 1910 is less likely to become tangled or get in the way than a longer Umbilical 1910 might.

Figure 19B:
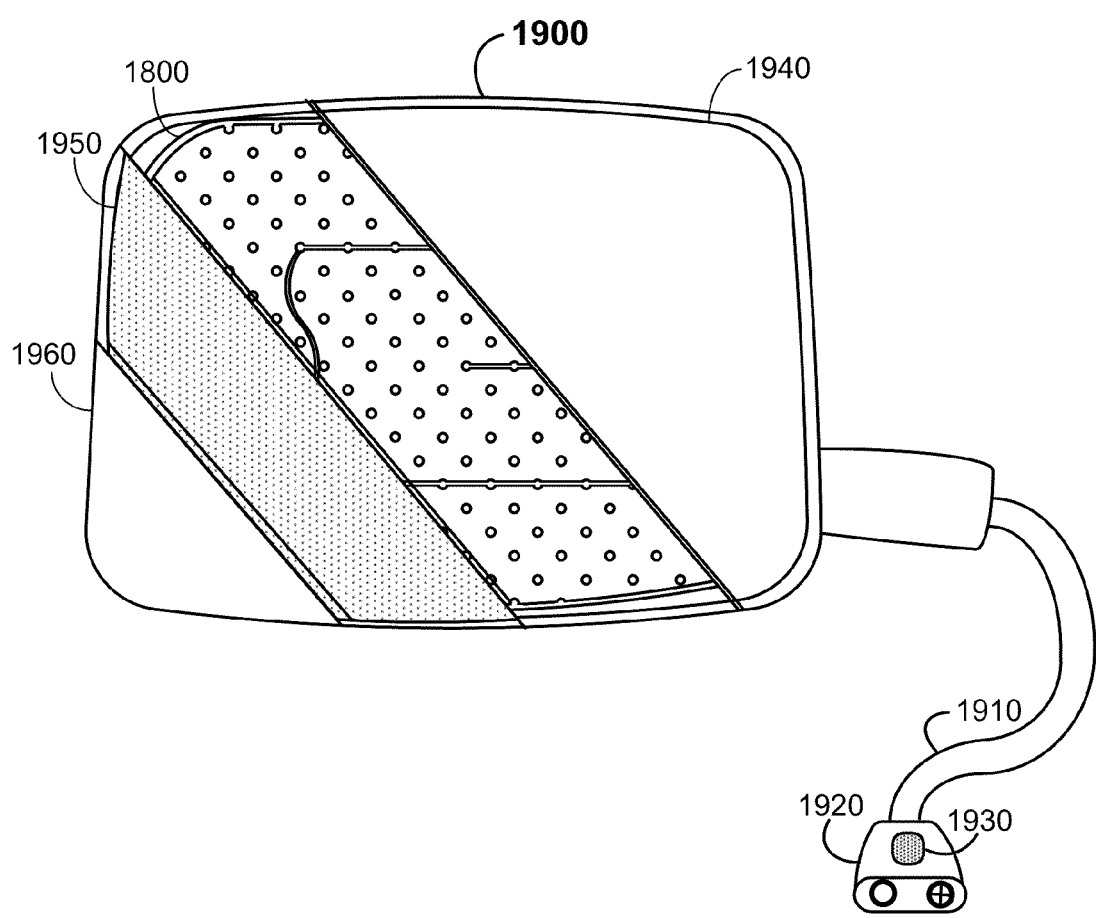
FIG. 19B illustrates a cutaway view of the interchangeable lumbar contrast therapy pad in accordance with an embodiment of the present invention.

Specifics of the Interchangeable Lumbar Contrast Therapy Pad 1900 may be further seen in reference to FIG. 19B. Here a cutaway view of the Interchangeable Lumbar Contrast Therapy Pad 1900 is illustrated. The first layer on the Interchangeable Lumbar Contrast Therapy Pad 1900, in relation to the wearer's body, may include a Mesh 1940 or other suitable surface material. This layer, in some embodiments, should be adapted to provide heat transfer between the Therapy Bladder 1800 and the user. Likewise, softness/comfort of this layer is critical, as the material may be adjacent the user's skin for prolonged periods of time. Other factors that are important in deciding the material to be used for this layer include breathability, ease of cleaning, cost and microbial properties.

Under the Mesh 1940 layer is the Therapy Bladder 1800. The Therapy Bladder 1800 is typically contained within a pocket formed by the Mesh 1940 and subsequent layers. The Umbilical 1910 couples to the Inlet Tube 1810 and Outlet Tube 1820 of the Therapy Bladder 1800.

After the Therapy Bladder 1800, a Cushion Layer 1950 may be seen. The Cushion Layer 1950 may provide a number of functions, including: comfort, support and compression. The Cushion Layer 1950 also provides a foundation for the Therapy Bladder 1800 thereby minimizing the chances of constrictions in the Therapy Bladder 1800 which may lead to reduced fluid flow. The Cushion Layer 1950 may include any number of materials, such as wool, cotton, down, closed cell foam, memory rubber, gel, or other padding material.

The last layer of the Interchangeable Lumbar Contrast Therapy Pad 1900 may include an exterior rear facing of Loop Material 1960. This enables the Interchangeable Lumbar Contrast Therapy Pad 1900 to be placed within the Rigid Back Support System 2000 and held in place with hook material. All layers of the Interchangeable Lumbar Contrast Therapy Pad 1900 may be held together through glue, welding or stitching. In some embodiments, a peripheral seam may couple the various layers together.

Figure 20A:
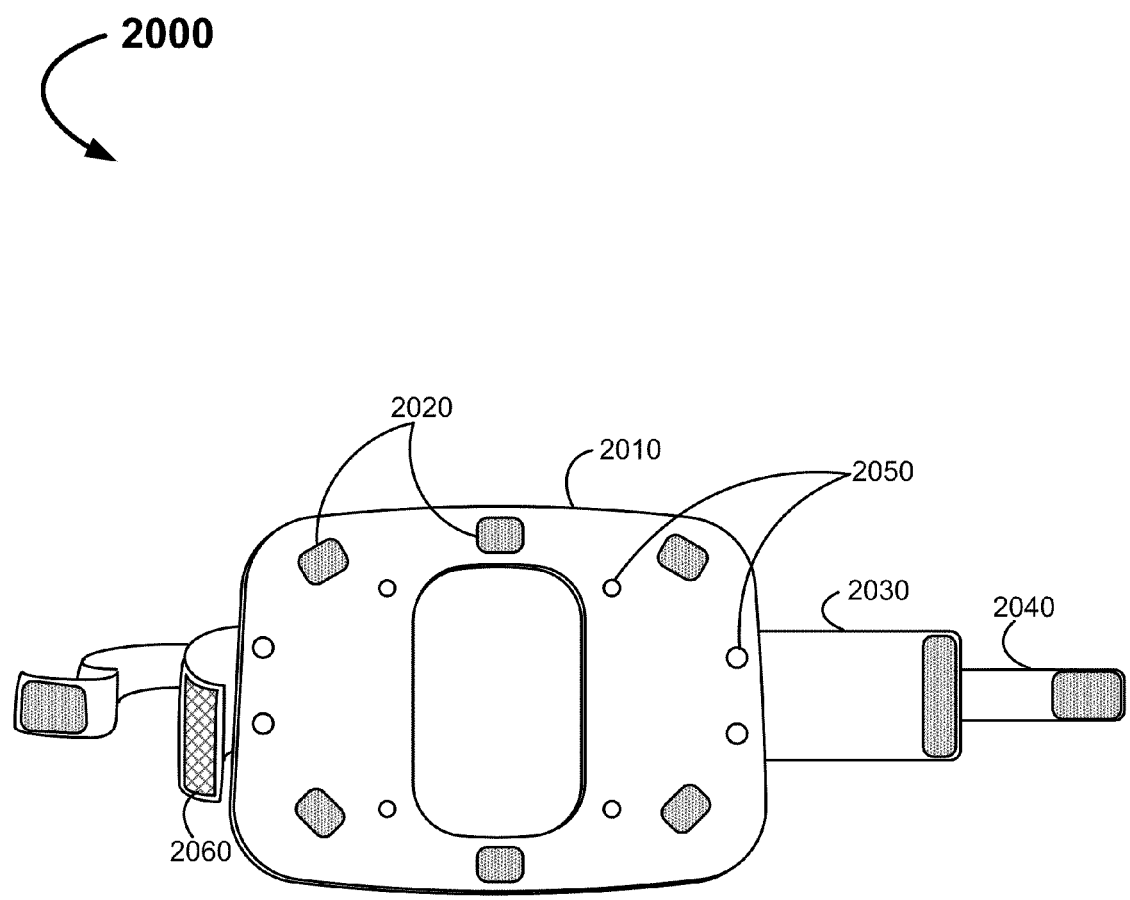
FIG. 20A illustrates an interior view of a rigid back support system configured to receive the interchangeable lumbar contrast therapy pad in accordance with an embodiment of the present invention.

Continuing to FIG. 20A, an interior view of the Rigid Back Support System 2000 configured to receive the Interchangeable Lumbar Contrast Therapy Pad 1900 is provided. The Rigid Back Support System 2000 includes a Rigid Back Member 2010. The degree of rigidity of the Rigid Back Member 2010 may be determined by material type, density, thickness and/or geometry. In some embodiments, the Rigid Back Member 2010 may be comprised of 3 mm thick contoured polyethylene. Of course, other plastics or other semi-rigid materials may be utilized for the construction of the Rigid Back Member 2010. Additionally, the Rigid Back Member 2010 may include composite materials, such as laminates in order to provide the desired rigidity and weight. Additionally, the Rigid Back Member 2010 may be designed to be more or less flexible in particular directions and orientations. Thus, vertical rigidity may be maintained, but torsion movement may be relatively flexible.

Also, in some embodiments, the Rigid Back Member 2010 may include an opening, or other cutout, in order to reduce overall weight and to promote airflow to the wearer. Hook material Pads 2020 may be coupled to the Rigid Back Member 2010. These hook material Pads 2020 may be located in such a way as to receive the Loop Material 1960 of the Interchangeable Lumbar Contrast Therapy Pad 1900.

Various Straps 2030 and 2040 may extend from the Rigid Back Member 2010. The Wide Strap 2030 may include elastic material such that the Rigid Back Support System 2000 may be wrapped to the wearer's body tightly. The width of the Wide Strap 2030 as well as the elasticity of the material used may be tailored in order to have straps which provide the desired level of tension around the user's body. The end of the Wide Strap 2030 may include a pad of hook material on one side, and a pad of Loop Material 2060 on the reverse side. The Hook material may be utilized to attach the Wide Strap 2030 to the front rigid support panel at a desired tightness. Similarly, The Narrow Straps 2040 may include some elastic components in order to modify the desired tightness of the brace. As with the Wide Strap 2030, the Narrow Straps 2040 may include hook material pads at their ends in order to connect them to the front rigid support panel. The Straps may be coupled to the Rigid Back Member 2010 via a series of Rivets 2050. Of course, alternate methods of coupling the straps to the Rigid Back Member 2010 are considered by the present invention.

Figure 20B:
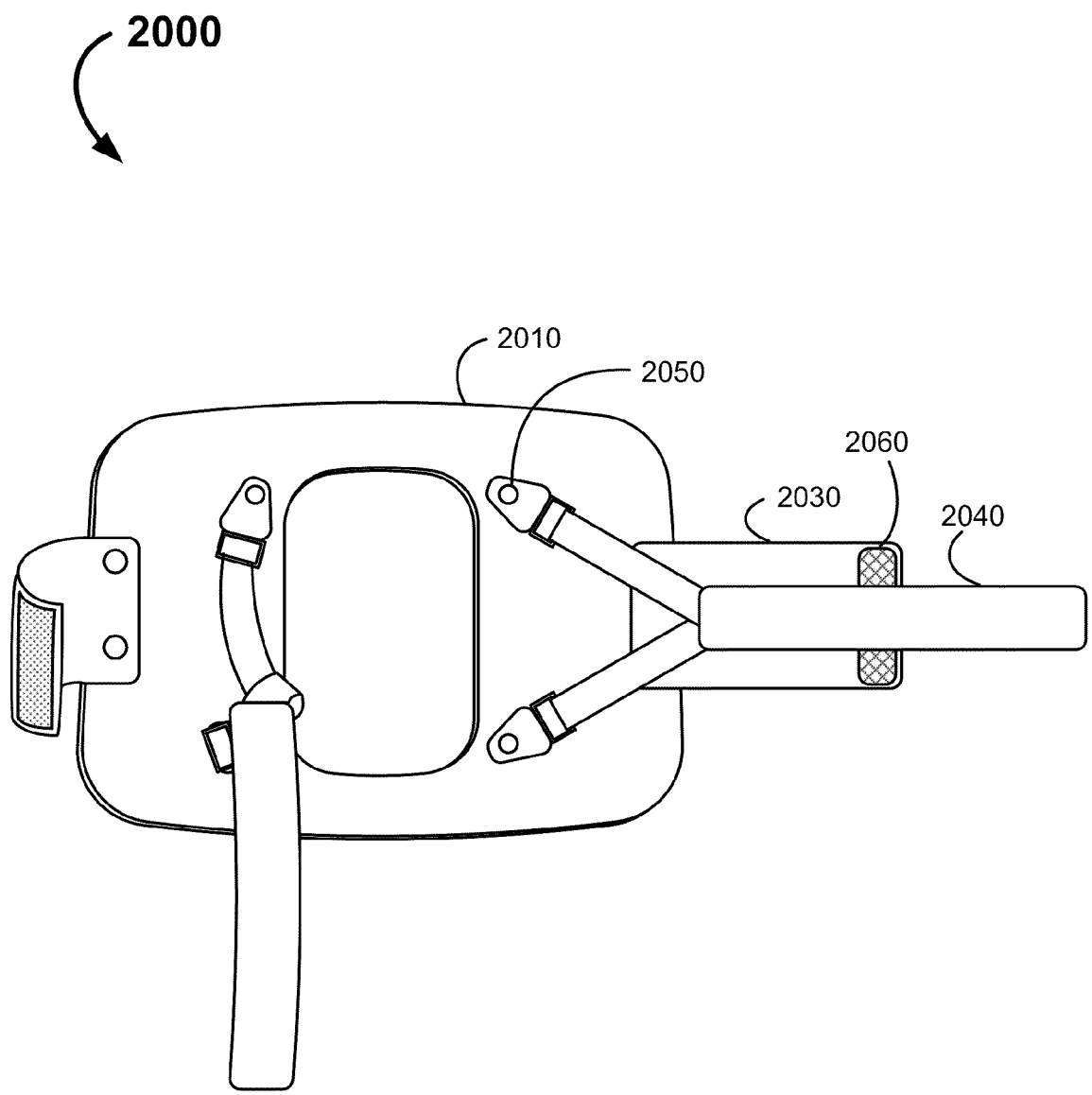
FIG. 20B illustrates a dorsal view of the rigid back support system configured to receive the interchangeable lumbar contrast therapy pad in accordance with an embodiment of the present invention.

FIG. 20B illustrates a dorsal view of the Rigid Back Support System 2000. This is the surface that may be seen when the brace is being worn by the user. Again, the Rigid Back Member 2010 may be seen. The Wide Straps 2030 may be seen riveted to the edge of the Rigid Back Member 2010. The connections for the Narrow Straps 2040, on the other hand, may occur closer to the center of the Rigid Back Member 2010. Again, Rivets 2050 facilitate this connection; however, the Narrow Straps 2040 may couple to an intermediate plastic hanger which enables rotation of the straps in relation to the Rigid Back Member 2010. The X-like design of the Narrow Straps 2040 enables a more form-hugging fit when the brace is worn by the user.

Figure 21:
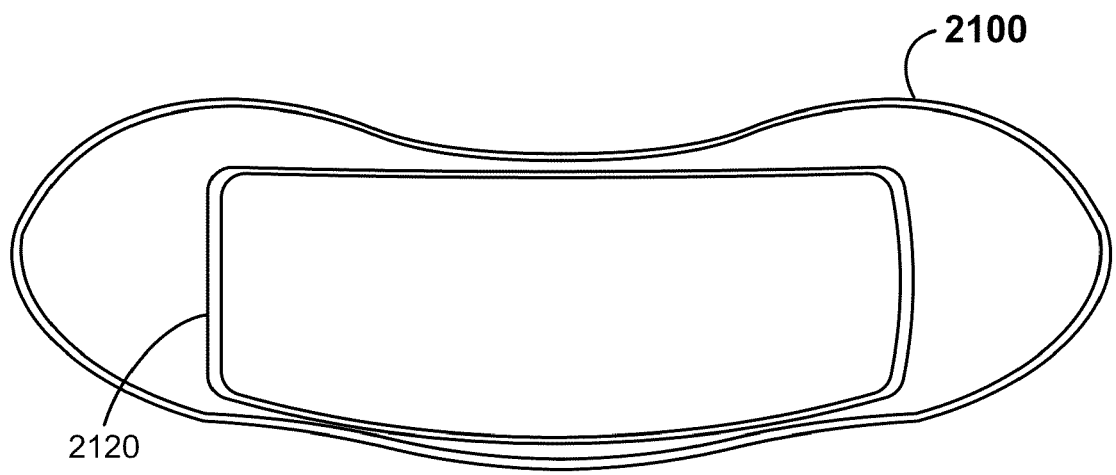
FIG. 21 illustrates a rigid frontal support configured to couple to the rigid back support system in accordance with an embodiment of the present invention.

FIG. 21 illustrates a Rigid Frontal Support Panel 2100 configured to couple to the Rigid Back Support System 2000 in accordance with an embodiment of the present invention. The Rigid Frontal Support Panel 2100 may be composed of loop like material so that the hook pads on the ends of the straps may directly couple to the Rigid Frontal Support Panel 2100. The Rigid Frontal Support Panel 2100 may also include a Pocket 2120 which may be configured to receive a contoured sheet of rigid material. This provides the entire Rigid Frontal Support Panel 2100 some degree of rigidity and stomach support for the wearer.

The rigid sheet may be removable to facilitate cleaning of the Rigid Frontal Support Panel 2100. Additionally, various rigid sheets may be substituted in the Rigid Frontal Support Panel 2100 in order to meet the user's desired support level. As with the back rigid support, the rigid sheet may include any single or composite material. However, in some embodiments, 3 mm polyethylene contoured sheeting may be particularly useful material due to its cost and physical properties.

Figure 22:
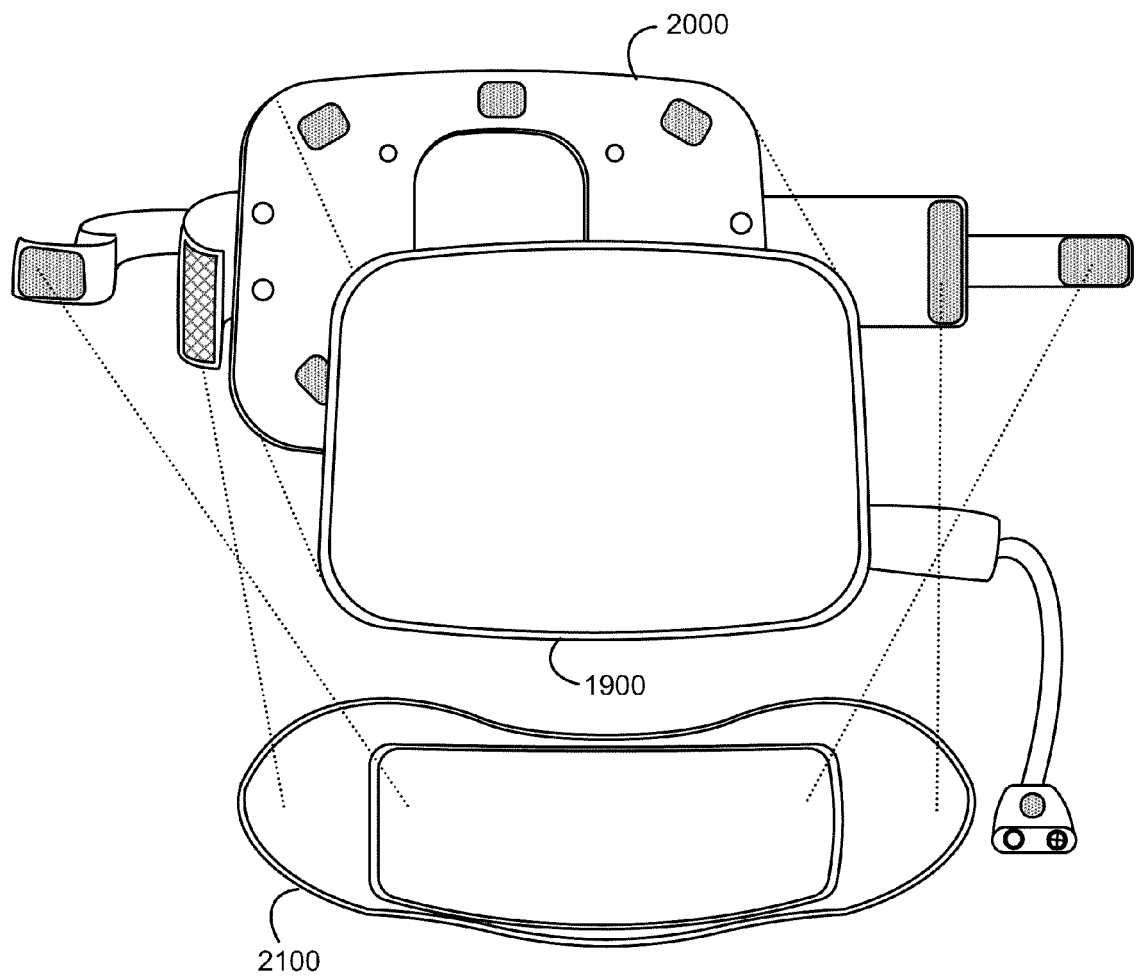
FIG. 22 illustrates a spinal column brace including the interchangeable lumbar contrast therapy pad, the rigid frontal support, and the rigid back support system, in accordance with an embodiment of the present invention.

Lastly, FIG. 22 illustrates the second embodiment spinal column brace as it is intended to be worn. The Interchangeable Lumbar Contrast Therapy Pad 1900 may couple to the Rigid Frontal Support Panel 2100 via the hook and loop material. This assembly may then be applied to the user's lower back. The Rigid Frontal Support Panel 2100 may be placed upon the user's stomach below the belly button. The Wide Straps 2030 and Narrow Straps 2040 may then loop around the side of the wearer to attach to the surface of the Rigid Frontal Support Panel 2100. The degree of tension placed on these straps then dictates the tightness of the brace when worn by the user.

The present invention can also be practiced with other techniques for providing thermal or contrast therapy to a therapy recipient and spinal column support. For example, it is possible, using the Spinal Column Brace with an interchangeable lumbar contrast therapy pad of the instant invention, to provide compression and thermal therapy to the therapy recipient without providing any additional external support, or the system may be configured to incorporate massage pads for massage therapy at the therapy site.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A spinal column brace system including an interchangeable contrast therapy pad, useful in association with a spinal column therapy recipient, the spinal column brace system comprising:
    a rigid support including a plurality of hook material patches, wherein the rigid support is coupled to a plurality of straps, wherein at least some portion of each strap of the plurality of straps is elastic, and wherein the plurality of straps includes a pad of hook material substantially near a terminus of each of the plurality of straps;
    an interchangeable therapy pad comprising a fluid bladder and a cushion layer, wherein the interchangeable therapy pad includes at least one surface covered in loop material configured to reversibly couple to the hook material of the rigid support;
    a front panel, wherein the front panel has at least one surface covered in loop material configured to reversibly couple to the pads of hook material located on the plurality of straps; and
    wherein the interchangeable therapy pad coupled to the rigid support coupled to the front panel is configured to circumvent the torso of the spinal column therapy recipient, and wherein the interchangeable therapy pad is in a fitted position adjacent a spinal column therapy site of the spinal column therapy recipient.

2. The spinal column brace system of claim 1, wherein the fluid bladder is a thermal exchange bladder.

3. The spinal column brace system of claim 2, wherein the thermal exchange bladder is coupled to a contrast therapy system, that includes a hot reservoir for holding a relatively hot fluid, a cold reservoir for holding a relatively cold fluid, a mixing valve for receiving a selected ratio of the hot and cold fluids from the hot and cold reservoirs and operable to deliver a therapy fluid with a therapy temperature determined by the selected ratio, and a fluid pump for delivering the therapy fluid to the thermal exchange bladder.

4. The spinal column brace system of claim 3, wherein the pump causes constant pressure within the thermal exchange bladder, wherein the constant pressure produces steady compression on the therapy site, and wherein the rigid support and front panel cause compression of the thermal exchange bladder on the therapy site of the user.

5. The spinal column brace system of claim 3, wherein the pump causes dynamic pressure within the thermal exchange bladder, wherein the dynamic pressure produces pulsating compression on the therapy site.

6. The spinal column brace system of claim 1, wherein rigid support is a contoured sheet of semi-rigid material less than five millimeters in thickness.

7. The spinal column brace system of claim 6, wherein the rigid support includes at least one cutout to reduce weight.

8. The spinal column brace system of claim 1, wherein the front panel further comprises a rigid member.

9. The spinal column brace system of claim 8, wherein the rigid member fits within a pocket located on the front panel.

10. The spinal column brace system of claim 8, wherein rigid member is a contoured sheet of semi-rigid material less than five millimeters in thickness.

* * * * *